US009027551B2

(12) United States Patent
King et al.

(10) Patent No.: US 9,027,551 B2
(45) Date of Patent: May 12, 2015

(54) DRY POWDER INHALERS THAT INHIBIT AGGLOMERATION, RELATED DEVICES AND METHODS

(71) Applicant: Oriel Therapeutics, Inc., Durham, NC (US)

(72) Inventors: Michael King, Durham, NC (US); Jeffrey Alan Warden, Raleigh, NC (US); Patrick D. Lopath, Stamford, CT (US); Richard D. LaRoche, Thetford Center, VT (US)

(73) Assignee: Oriel Therapeutics, Inc., Durham, NC (US)

( * ) Notice: Subject to any disclaimer, the term of this patent is extended or adjusted under 35 U.S.C. 154(b) by 101 days.

(21) Appl. No.: 13/734,323

(22) Filed: Jan. 4, 2013

(65) Prior Publication Data

US 2013/0152926 A1 Jun. 20, 2013

Related U.S. Application Data

(62) Division of application No. 11/575,178, filed as application No. PCT/US2005/032492 on Sep. 12, 2005, now Pat. No. 8,365,725.

(60) Provisional application No. 60/609,485, filed on Sep. 13, 2004.

(51) Int. Cl.
*A61M 15/00* (2006.01)
*B01F 5/06* (2006.01)

(52) U.S. Cl.
CPC ....... *A61M 15/0091* (2013.01); *Y10T 29/49826* (2015.01); *A61M 15/0086* (2013.01); (Continued)

(58) Field of Classification Search
CPC .............. A61M 15/00; A61M 11/002; A61M 15/0028; A61M 15/002; A61M 15/0045; A61M 15/0055; A61M 15/0043; A61M 15/0051; A61M 15/0086; A61M 11/003; A61M 15/0021; A61M 15/009; A61M 15/0091; A61M 15/0038; A61M 15/0036; A61M 15/0068; A61M 15/0008; A61M 15/0048; A61M 15/0065; A61M 16/00; A61M 15/001; B65D 83/04; B65D 83/0454; B65D 83/06; B67B 7/00; B67B 7/46; B67B 7/30; B01F 5/0619
USPC ............ 128/200.11–200.22, 200.24, 203.12, 128/203.15, 203.19, 203.21; 604/58, 93.01; 239/461, 466, 468, 487, 489, 472, 499, 239/371
See application file for complete search history.

(56) References Cited

U.S. PATENT DOCUMENTS 3,653,380 A 4/1972 Hansen
3,809,294 A 5/1974 Torgeson
(Continued)

FOREIGN PATENT DOCUMENTS

EP 0712637 5/1996
EP 1106196 6/2001
(Continued)

OTHER PUBLICATIONS

Assi et al. "The device resistance of recently introduced dry-powder inhalers" *J. Pharm. Pharmacol.* 52(Supplement):58 (2000).
(Continued)

*Primary Examiner* — Annette Dixon
(74) *Attorney, Agent, or Firm* — Myers Bigel Sibley & Sajovec, P.A.

(57) ABSTRACT

Inhalers with fins that deagglomerate dry powder using inspiratory effort of a user of an inhaler. The inhaler fins, at least in steady state conditions, are configured to generate dry powder and airflow patterns having turbulence with flow vortices, some of which may have a vortex having an axis of rotation that extends in an inspiratory flow direction while others may have a vortex that is substantially orthogonal to the inspiratory flow direction in an inspiratory airflow path, as an amount of dry powder travels through the inhaler to thereby deagglomerate the dry powder without trapping undue amounts of the dry powder during inhalation.

14 Claims, 17 Drawing Sheets

(52) U.S. Cl.
CPC .. *A61M2202/064* (2013.01); *A61M 2205/3569* (2013.01); *A61M 2205/3584* (2013.01); *A61M 2205/3592* (2013.01); *A61M 2206/14* (2013.01); *B01F 5/0619* (2013.01); *B01F 2005/0636* (2013.01); *A61M 15/001* (2014.02)

(56) References Cited

U.S. PATENT DOCUMENTS

| | | | |
|---|---|---|---|
| 3,897,779 | A | 8/1975 | Hansen |
| 3,948,264 | A | 4/1976 | Wilke et al. |
| 4,013,075 | A | 3/1977 | Cocozza |
| 4,047,525 | A | 9/1977 | Kulessa et al. |
| 4,706,663 | A | 11/1987 | Makiej |
| 4,907,583 | A | 3/1990 | Wetterlin et al. |
| 4,981,368 | A | 1/1991 | Smith et al. |
| 5,201,322 | A | 4/1993 | Henry et al. |
| 5,243,970 | A | 9/1993 | Ambrosio et al. |
| 5,304,125 | A | 4/1994 | Leith |
| 5,388,572 | A | 2/1995 | Mulhauser et al. |
| 5,460,173 | A | 10/1995 | Mulhauser et al. |
| 5,533,502 | A | 7/1996 | Piper |
| 5,582,162 | A * | 12/1996 | Petersson ............... 128/203.15 |
| 5,622,166 | A | 4/1997 | Eisele et al. |
| 5,647,347 | A | 7/1997 | Van Oort |
| 5,655,523 | A | 8/1997 | Hodson et al. |
| 5,669,378 | A | 9/1997 | Pera et al. |
| 5,676,130 | A * | 10/1997 | Gupte et al. ............ 128/203.19 |
| 5,727,607 | A | 3/1998 | Ichikawa et al. |
| 5,743,250 | A | 4/1998 | Gonda et al. |
| 5,909,829 | A | 6/1999 | Wegman et al. |
| 5,947,169 | A | 9/1999 | Wegman et al. |
| 5,954,047 | A * | 9/1999 | Armer et al. ............ 128/200.23 |
| 6,029,663 | A | 2/2000 | Eisele et al. |
| 6,065,472 | A * | 5/2000 | Anderson et al. ....... 128/203.21 |
| 6,116,238 | A | 9/2000 | Jackson et al. |
| 6,328,033 | B1 | 12/2001 | Avrahami |
| 6,347,629 | B1 | 2/2002 | Braithwaite |
| 6,367,471 | B1 * | 4/2002 | Genosar et al. .......... 128/200.23 |
| 6,681,768 | B2 | 1/2004 | Haaije de Boer et al. |
| 6,855,909 | B2 | 2/2005 | Patel et al. |
| 6,889,690 | B2 | 5/2005 | Crowder et al. |
| 6,923,175 | B2 | 8/2005 | Poole et al. |
| 6,971,383 | B2 | 12/2005 | Hickey et al. |
| 7,025,056 | B2 | 4/2006 | Eason et al. |
| 2001/0007853 | A1 | 7/2001 | Dimarchi et al. |
| 2001/0053761 | A1 | 12/2001 | Dimarchi et al. |
| 2003/0222364 | A1 | 12/2003 | Jackson et al. |
| 2004/0035412 | A1 | 2/2004 | Staniforth et al. |
| 2007/0221218 | A1 | 9/2007 | Warden et al. |

FOREIGN PATENT DOCUMENTS

| | | |
|---|---|---|
| EP | 1166812 | 1/2002 |
| WO | WO 99/13930 | 3/1999 |
| WO | WO 01/68169 | 9/2001 |

OTHER PUBLICATIONS

Chemineer "Kenics Products" *Chemineer: Mixers and Agitators* <www.chemineer.com/kenics_products.php> 1 page (2005).

Chemineer "Kenics HEV Static Mixers" *Chemineer Mixers and Agitators—HEV Static Mixers* 1 page (p. 1 of 2) (2005).

Clark et al. "The Relationship Between Powder Inhaler Resistance and Peak Inspiratory Conditions in Healthy Volunteers—Implications for In Vitro Testing" *Journal of Aerosol Medicine* 6(2):99-110 (1993).

Crowder et al. "2001: An Odyssey in Inhaler Formulation and Design" *Pharmaceutical Technology* 25(7):99-113 (2001).

Hickey et al. "A New Millennium for Inhaler Technology" *Pharmaceutical Technology* 21(6):116-125 (1997).

Kenics "HEV High Efficiency Static Mixer" *Chemineer, Inc., Bulletin 811* 2 pages (believed prior to Sep. 13, 2004).

Peart et al. "New Developments in Dry Powder Inhaler Technology" *American Pharmaceutical Review* 4(3):37-45 (2001).

Prime et al. "Review of dry powder inhalers" *Advanced Drug Delivery Reviews* 26:51-58 (1997).

Tilton et al. "Computer Simulation Yields $1 Million at DuPont by Improving Static Mixing" *Fluent* ww.fluent.com 4 pages (2001).

Wolff et al. "Generation of Aerosolized Drugs" *Journal of Aerosol Medicine* 7(1):89-106 (1994).

* cited by examiner

GENERATING A DRY POWDER AND AIR FLOW PATTERN HAVING FLOW VORTICES WITH AT LEAST ONE VORTEX HAVING AN AXIS OF ROTATION THAT EXTENDS IN AN INSPIRATORY FLOW DIRECTION IN AN INSPIRATORY AIRFLOW PATH, AS AN AMOUNT OF DRY POWDER TRAVELS THROUGH THE INHALER UPON PATIENT INSPIRATION TO THEREBY DEAGGLOMERATE THE DRY POWDER WITHOUT TRAPPING UNDUE AMOUNTS OF THE DRY POWDER IN THE INHALER DURING INHALATION.

10

GENERATING EDGE-INDUCED FLOW VORTICES FROM AT LEAST ONE POINT AND TWO LONG EDGES.

12

THE INSPIRATORY AIRFLOW PATH HAS A DEAGGLOMERATING PORTION THAT ENCLOSES AT LEAST ONE TURBULENCE PROMOTER, THE DEAGGLOMERATING PORTION HAVING A CROSS-SECTIONAL AREA THAT IS ABOUT 200 $mm^2$ OR LESS.

14

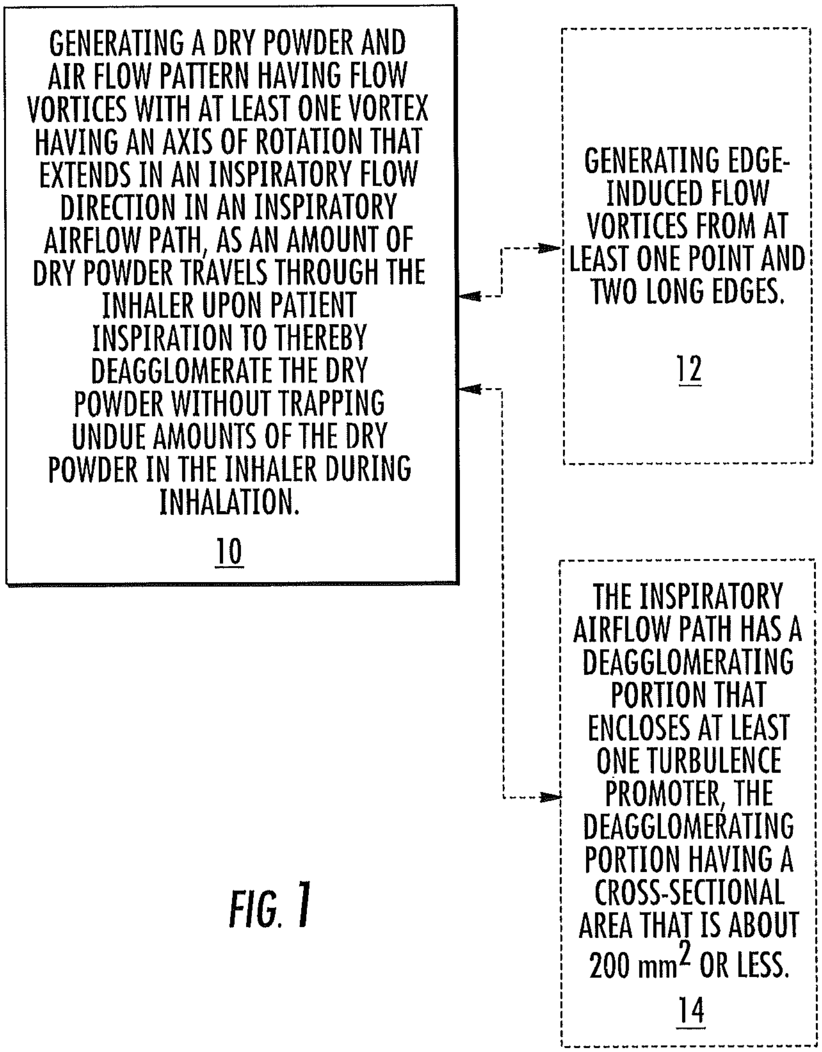

FIG. 1

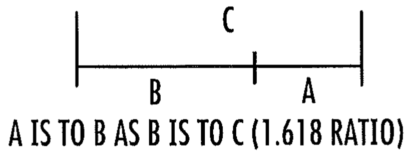
FIG. 14
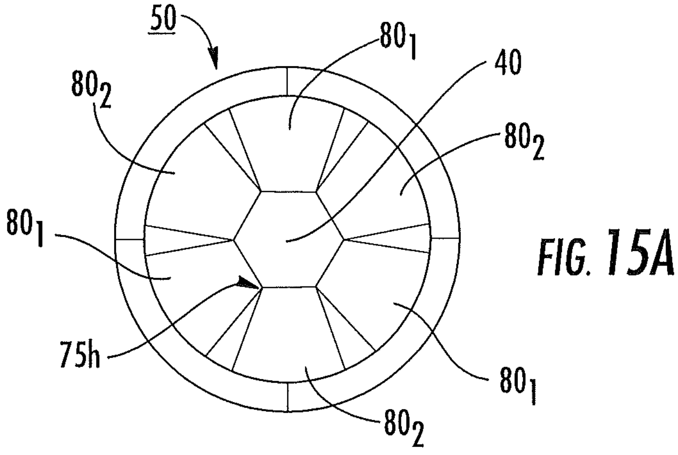
FIG. 15A
FIG. 15B
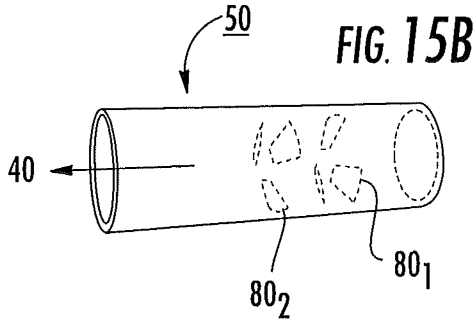

| fins | % airpath appearing blocked by fins/mesh (end view) | % airpath appearing open (end view) |
|---|---|---|
| design 1 @ 60° | 50.1 | 49.9 |
| design 1 @ 60°, offset | 77.9 | 22.1 |
| design 2 @ 30° | 23.0 | 77.0 |
| design 3 @ 60° | 25.3 | 74.7 |
| design 4 @ 60° | 37.4 | 62.6 |
| design 4 @ 60°, offset | 74.8 | 25.2 |
| design 4 @ 30° | 37.4 | 62.6 |
| hex mesh, coarse | 15.2 | 84.8 |
| hex mesh, fine | 22.0 | 78.0 |
| mesh design 1, coarse | 21.8 | 78.2 |
| mesh design 1, fine | 30.3 | 69.7 |
| mesh design 2, coarse | 23.4 | 76.6 |
| mesh design 2, fine | 30.4 | 69.6 |
| cone mesh design 1, fine | 30.4 | 69.6 |
| cone mesh design 2, coarse | 23.4 | 76.6 |
| no fins | 0.0 | 100.0 |

DRY POWDER INHALERS THAT INHIBIT AGGLOMERATION, RELATED DEVICES AND METHODS

RELATED APPLICATIONS

This application is a divisional application of U.S. patent application Ser. No. 11/575,178, which is a 35 USC 371 national phase application of PCT/US2005/032492, filed Sep. 12, 2005, which claims the benefit of priority from U.S. Provisional Patent Application Ser. No. 60/609,485, filed Sep. 13, 2004, the contents of which are hereby incorporated by reference as if recited in full herein.

FIELD OF THE INVENTION

The present invention relates to drug containment and/or dispensing systems suitable for dry powders formulated for delivery as inhalant aerosols.

BACKGROUND OF THE INVENTION

Dry powder inhalers (DPIs) represent a promising alternative to pressurized pMDI (pressurized meted dose inhaler) devices for delivering drug aerosols without using CFC propellants. See generally, Crowder et al., 2001: *an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients.

Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form of the dry powder (such as a particulate size) into a patient's airway and direct it to a desired deposit site(s).

A number of obstacles can undesirably impact the performance of the DPI. For example, the small size of the inhalable particles in the dry powder drug mixture can subject them to forces of agglomeration and/or cohesion (certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, some dry powder inhalers can retain a significant amount of the drug within the device, which can be especially problematic over time.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of all of these patents are hereby incorporated by reference as if stated in full herein.

More recently, Hickey et al., in U.S. patent application Ser. No. 10/434,009 and PCT Patent Publication No. WO 01/68169A1 and related U.S. National Stage patent application Ser. No. 10/204,609, have proposed a DPI system to actively facilitate the dispersion and release of dry powder drug formulations during inhalation using piezoelectric polymer film elements which may promote or increase the quantity of fine particle fraction particles dispersed or emitted from the device over conventional DPI systems. The contents of these documents are hereby incorporated by reference as if recited in full herein.

Notwithstanding the above, there remains a need for alternative inhalers and/or blister packages that can be used with dry powder inhalers.

SUMMARY OF EMBODIMENTS OF THE INVENTION

In some embodiments, inhalers comprise turbulence promoters that can generate flow patterns and/or interact with air and dry powder to deagglomerate the dry powder upon inspiration by a user. The flow patterns may include flow vortices of air and dry powder.

Some embodiments are directed to methods of deagglomerating dry powder using inspiratory effort of a user of an inhaler. The methods include generating a dry powder and air flow pattern having flow vortices, at least one vortex having an axis of rotation that extends axially in an inspiratory flow direction and at least another having a shedding vortex in an inspiratory airflow path as an amount of dry powder travels through the inhaler upon patient inspiration to thereby deagglomerate the dry powder without trapping undue amounts of the dry powder during inhalation.

In some embodiments, the generating step may be carried out using a plurality of spaced apart statically configured turbulence promoters that reside in the inspiratory airflow path, each defining at least one point and two edge portions that create respective point and edge-induced flow vortices.

Some embodiments are directed to methods of deagglomerating dry powder in a dry powder inhaler. The methods can include generating a dry powder and air flow pattern having flow vortices using at least one turbulence promoter that extends across at least a portion of an inspiratory flow path.

The at least one turbulence promoter can be configured to generate at least some flow vortices having an axis of rotation that extends axially in an inspiratory flow direction in the inspiratory airflow path and at least some flow vortices having an axis of rotation that is substantially perpendicular to the inspiratory flow direction to thereby facilitate deagglomeration of the dry powder without trapping undue amounts of the dry powder in the inhaler.

In some embodiments, the airflow path has a deagglomerating portion that encloses the turbulence promoters, the deagglomerating portion having a cross-sectional area that is about 200 $mm^2$ or less and in some particular embodiments, the deagglomerating portion of the inspiratory airflow path can have a cross-sectional width that is about 12 mm or less and may have a length that is less than about 1 inch.

Other embodiments are directed to inhalers that have: (a) an inhaler body with an inspiratory flow path therein; and (b) at least one turbulence promoter residing in the inspiratory flow path, the at least one turbulence promoter comprising at least one point or edge configured to generate a flow vortex of air and dry powder in response to inspiratory effort by a user.

Some embodiments are directed to dry powder inhalers that include: (a) an inhaler body with an inspiratory flow path therein; and (b) at least one turbulence promoter residing in the inspiratory flow path, the at least one turbulence promoter comprising at least two edges that converge to define a point. The at least one turbulence promoter can be configured to generate a plurality of point-induced and edge-induced flow vortices of air and dry powder in response to inspiratory effort by a user, whereby some of the flow vortices have an axis of rotation that extends in an inspiratory flow direction and some of the flow vortices have an axis of rotation that is substantially orthogonal to the inspiratory flow direction.

In some embodiments, the turbulence promoters comprise ramped fins that extend angularly inward at an acute angle from a bounding surface in a direction of flow into an inspiratory flow path to deagglomerate the dry powder without unduly trapping dry powder particulates.

The fins can have at least one sharp outer tip and long edges that create respective flow vortices and provide for cross-stream turbulence to deagglomerate the dry powder as the dry powder travels along the inspiratory flow path. A plurality of circumferentially spaced apart fins can be arranged in axially spaced apart series.

Other embodiments are directed to inserts sized and configured for insertion into a dry powder inhaler, the insert having a plurality of spaced apart fins ramped from a bounding surface toward an axial centerline of the inhaler.

Still other embodiments are directed to methods of fabricating a dry powder inhaler to provide deagglomeration during inspiratory effort. In some embodiments, the methods include providing an insert having at least one fin extending angularly inward from a bounding surface; and placing the insert into an inspiratory airflow path of an inhaler.

In other embodiments, the methods can include (injection or otherwise) molding at least one fin extending angularly inward from a bounding surface into an inspiratory airflow path of an inhaler.

Some embodiments are directed to methods of fabricating an insert for an inhaler comprising photochemical etching a mesh pattern of shapes with points and long edges into a substrate.

Other dry powder inhalers include: (a) an inhaler body with an inspiratory flow path therein; and (b) a plurality of axially spaced apart fins that incline inwardly at an acute angle in a primary direction of flow from a bounding surface so that a respective fin occupies a subportion of a cross-sectional width of the inspiratory flow path. The at least one fin having a body portion with at least two edges that meet to define at least one point, the edges and point residing in the inspiratory flow path. The at least one fin is configured to deagglomerate dry powder in response to inspiratory effort by a user.

Some dry powder inhalers include: (a) an inhaler body with an inspiratory flow path therein; and (b) at least one mesh body residing in the inspiratory flow path. The at least one mesh body having a pattern of shapes that define two edges that meet at a point, the mesh body extending across at least a major portion of the inspiratory flow path to facilitate deagglomeration of dry powder as the dry powder flows through the mesh in response to inspiratory effort by a user.

The mesh body can be substantially planar and may be oriented to angle in an axial flow direction.

In some other embodiments, the mesh body has a three-dimensional shape in the inspiratory flow path, such as an elongate spiral, generally concave or generally conical shape.

Other embodiments are directed to dry powder inhalers that include: an inhaler body with an inspiratory flow path therein; and at least one conical mesh body residing in the inspiratory flow path. The at least one mesh body has at least one of shaped open cells or closed shapes that define edges to thereby deagglomerate dry powder as the dry powder flows through the mesh in response to inspiratory effort by a user.

Some embodiments are directed to dry powder inhalers that include: (a) an inhaler body with an inspiratory flow path therein; and (b) a plurality of fins that, in position, have a body with an elongate axial cross-section. The fins have a transverse cross-sectional width that is a minor portion of an axial length of the fin. The fins have a trailing edge defining a wingtip. When viewed in transverse cross section, the fins extend from a bounding surface a distance into the inspiratory airflow path, the distance being a sub-portion of a cross-sectional width of the inspiratory path whereby the fins deagglomerate dry powder in response to inspiratory effort by a user.

Still other embodiments are directed to dry powder inhalers that include: (a) an inhaler body with an inspiratory flow path therein; and (b) at least one substantially conical or substantially concave mesh body residing in the inspiratory flow path. The at least one mesh body includes at least one of shaped open cells or closed shapes that define points to thereby facilitate deagglomeration of dry powder as the dry powder flows through the mesh in response to inspiratory effort by a user.

Other embodiments of dry powder inhalers include: (a) an inhaler body with an inspiratory flow path therein; and (b) a plurality of fins that incline inwardly at an acute angle in a primary direction of flow from a bounding surface so that a respective fin occupies a subportion of a cross-sectional width of the inspiratory flow path. The at least one fin having a forward generally triangular body portion with two long edges that meet to define at least one point. The point residing at the trailing portion of the fin body in the inspiratory flow path to thereby deagglomerate dry powder in response to inspiratory effort by a user.

Still other embodiments are directed to dry powder inhalers that include: an inhaler body with an inspiratory flow path therein; and at least one spiral mesh body residing in the inspiratory flow path. The at least one spiral mesh body has open cell shapes with points whereby in response to inspiratory effort by a user dry powder and air flow interact with the spiral mesh body to deagglomerate dry powder.

It is noted that aspects of the invention may be embodied as hardware, software or combinations of same, i.e., devices and/or computer program products. These and other objects and/or aspects of the present invention are explained in detail in the specification set forth below.

BRIEF DESCRIPTION OF THE FIGURES

FIG. 1 is a flow chart of exemplary operations that can be used to carry out embodiments of the present invention.

FIG. 14 is a schematic illustration of a scale illustrating a mathematical relationship of proportions.

FIG. 15A is an end view of an inspiratory airflow path according to embodiments of the present invention.

FIG. 15B is a side view illustrated to show internal fins arranged as shown in FIG. 15A according to embodiments of the present invention.

FIG. 31 is a listing of Table 1 of Fin and Mesh data according to embodiments of the present invention.

DESCRIPTION OF EMBODIMENTS OF THE INVENTION

Figure 2A:
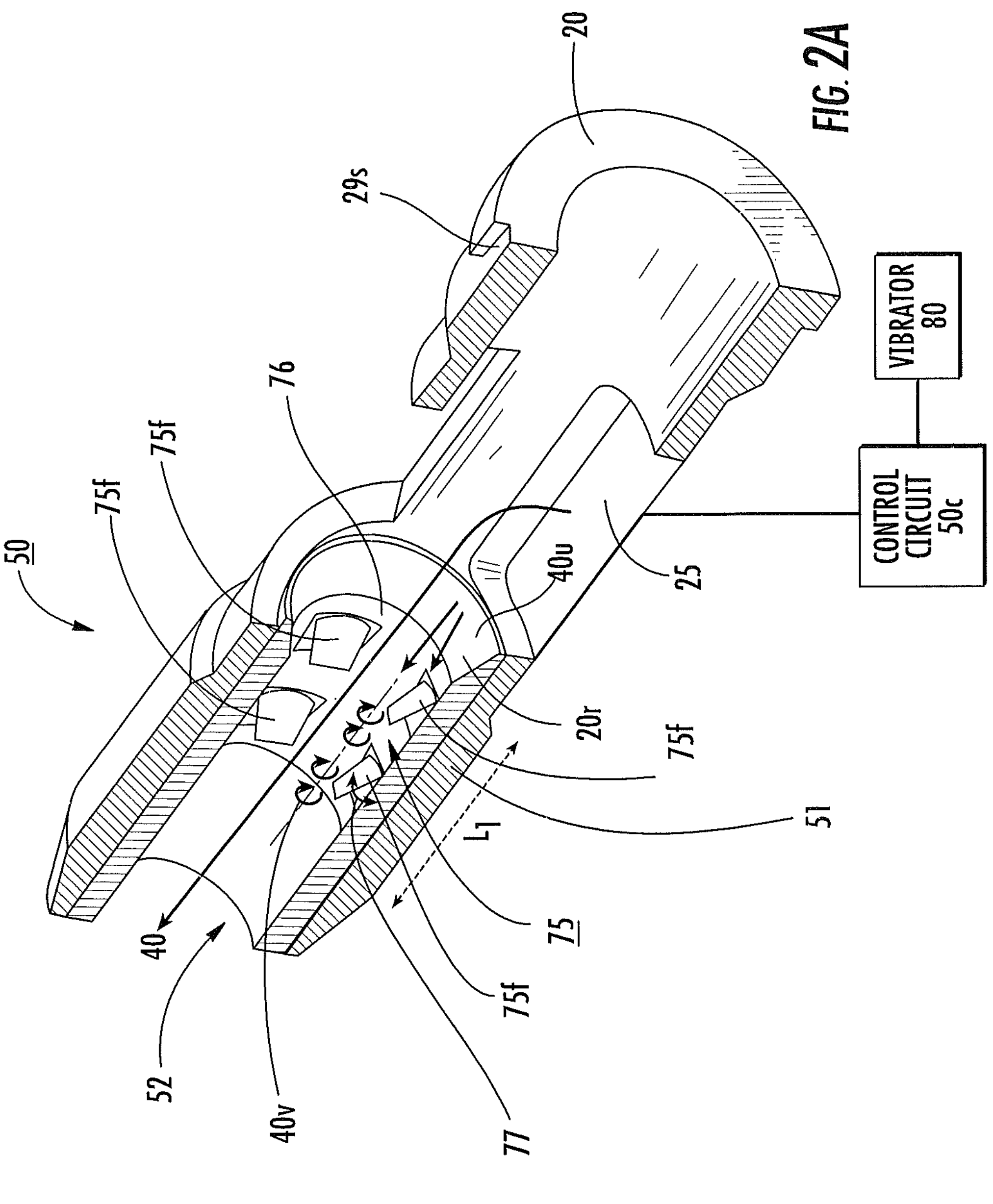
FIG. 2A is an enlarged, perspective, axial section view of an inhaler device according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "drug container package" describes a disposable drug container device that holds at least one unitized, meted and/or bolus amount of a target drug or medicament and may be also known as a drug containment system ("DCS"). The term "sealant layer" and/or "sealant material" includes configurations that have at least one layer or one material; thus, such a phrase also includes multi-layer or multi-material sealant configurations. The term "unitized" means a specified quantity of a pharmaceutical drug and/or medicament in terms of which the magnitudes of other quantities of the same or different drug and/or medicament can be stated.

The term "fin" means a protruding member that resides in the inspiratory air and dry powder flow path (typically downstream of a DCS or dry powder entry location) to promote turbulence and/or otherwise facilitate deagglomeration. The fin may be formed integral to the flow path or may be provided as a subassembly and/or a discrete component. A fin can have at least one point and two long edges (typically straight edges). The two long edges can converge to a corner to define the point.

The term "deagglomeration" and its derivatives refer to processing dry powder in the inhaler airflow path to inhibit the dry powder from remaining or becoming agglomerated or cohesive during inspiration. The term "mesh" means a material or member with open spaces. The mesh may take the form of joined, spaced apart, closed shapes or open shapes to provide a network of open spaces. The mesh may be rigid or resiliently configured. The closed shapes or open spaces may be regularly spaced or irregularly spaced.

The terms "conical" and "cone-like" mean that the referenced shape visually resembles a cone but is not intended to be overly formal and such a shape is not required to meet the mathematical definition of a cone. Generally stated, a shape is "conical" or "cone-like" when lines projected from the bounds of the shape axially converge to a vertex even though the body forming such a shape may be discontinuous or terminate before a cone is actually formed. The terms are also intended to include frustoconical shapes. The term "spiral" refers to a shape that resembles a spiral such that its body axially turns, coils or winds over its length at a varying or constant distance from a central axis. The term "substantially triangular" means that the shape is not a straight edge triangle but resembles a triangular shape and has at least two long edges that meet at a corner or point that is positioned the furthermost distance from an outer boundary surface into the airflow path.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 $g/cm^3$ or less. In particular embodiments, the low-density powder may have a density of about 0.5 $g/cm^3$ or less. The dry powder may be a dry powder with cohesive or agglomeration tendencies.

In any event, individual dispensable quantities of dry powder formulations can be a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroid, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled *Method for Administering ASPB28-Human Insulin* and U.S. Patent Application Publication No. 20010007853, entitled *Method for Administering Monomeric Insulin Analogs*, the contents of which are hereby incorporated by reference as if recited in full herein.

Typical dose amounts of the unitized dry powder mixture dispersed in the inhalers may vary depending on the patient size, the systemic target, and the particular drug(s). A conventional exemplary dry powder dose amount for an average adult is less than about 50 mg, typically between about 10-30 mg and for an average adolescent pediatric subject is typically from about 5-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

FIG. 1 illustrates a method of facilitating deagglomeration of a dry powder in an inhaler by generating a dry powder and airflow pattern having flow vortices that generate turbulence without unduly trapping dry powder and to provide an appropriate inspiratory resistance. It is currently believed that one or more (or a combination of) the below features may promote deagglomeration in transient flow operation:

(a) a flow pattern that has at least one tip-induced vortex;

(b) a flow pattern that has at least one edge-induced vortex;

(c) an area of cross section blocked by the fins (the "effective area" or what appears to be blocked when looking straight down or in an end view of the airpath);

(d) turbulence, including peak turbulence achieved and a portion of the airpath cross-section over which turbulent flow exists (turbulence is defined by a Reynolds number (Re) >4000). It is believed that the higher the Reynolds number, the higher the shear forces are in the flow. One parameter that may be a good indicator of deagglomeration is turbulent kinetic energy or turbulent dissipation rather than simply the Re number (or with the Re number));

(e) impaction, the deagglomerating member (such as fins) are obstructions in the airpath with which at least some particles can collide, break up and continue down the airpath; and (f) indirect airpath, at least some of the particles should flow in a non-straight path through the airpath because of the (partially) blocking deagglomerating member or turbulence promoter which may help break up the agglomerates. The amount of particles that may be configured to flow in an offset (non-straight) path can be a minor portion (such as between about 10% to less than about 50%) of the dry particles, at least about major portion (such as about 50-55%), or greater than a major portion (such as between about 55%-75%). However, not all the particles are required to flow in the non-straight path as resistance may be unduly increased.

Dry powder inhalers according to the present invention can use deagglomeration members that are turbulence promoters that are designed to provide appropriate airpath resistance, inhibit powder deposition (trapping) and provide a suitable FPF. The term "FPF" refers to fine particle fraction, which is well known to those of skill in the field of inhalers.

In some embodiments (when analyzed in a steady state flow), at least one vortex can be generated to have an axis of rotation that extends in an inspiratory flow direction in an inspiratory airflow path, as an amount of dry powder travels through the inhaler upon patient inspiration, to thereby deagglomerate dry powder without trapping undue amounts of the dry powder in the inhaler during inhalation (block 10).

In some embodiments, the vortices can include tip and edge-induced swirling flow vortices generated by at least one point and two edges of a fin or other member that is disposed in the inspiratory airflow path (block 12).

In at least steady state flow conditions, the edge induced flow vortices can be shedding flow vortices and the point induced flow vortices can reduce the size of their rotational shape as the airflow and dry powder flow axially downstream of the generation loci.

The inspiratory airflow path can have a deagglomerating segment 51 (FIG. 2A) that encloses at least one turbulence promoter 75 and has a relatively small (transverse) cross sectional area, typically less than about of about 200 $mm^2$ or less, and more typically less than about 100 $mm^2$. In some embodiments, the cross-sectional width or diameter can be less than about 12 mm, such as about 10 mm, about 8 mm, or about 6 mm. The deagglomerating segment 51 can be relatively short with a length ($L_1$) that is less than about 2 inches (5.08 cm), typically less than about 1.5 inches (3.81 cm), and more typically less than about 1 inch (2.54 cm). In some particular embodiments, the deagglomerating segment 51 has a length that is between about 0.1 to about 0.5 inches.

Figure 3:
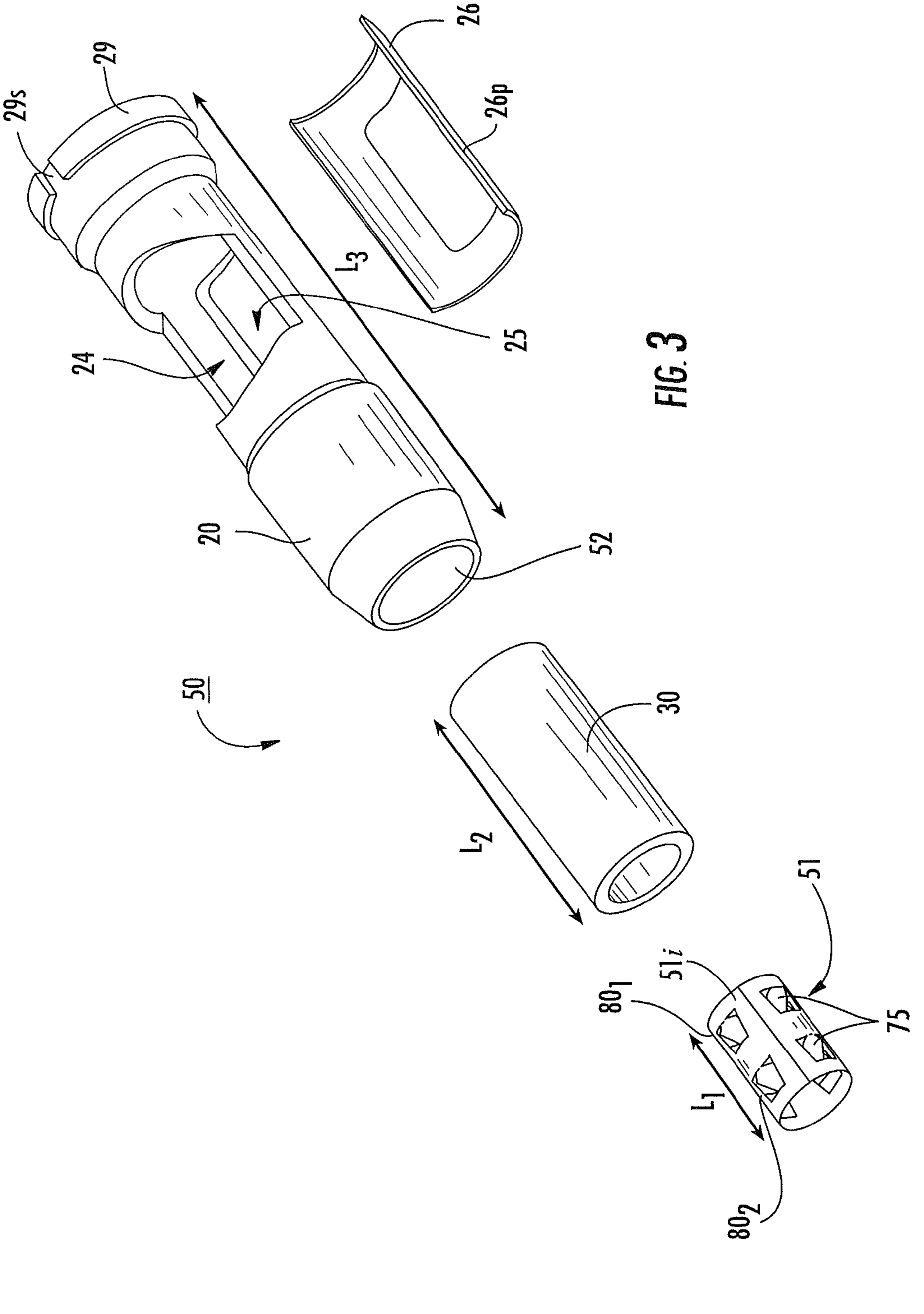
FIG. 3 is an exploded perspective view of the device shown in FIGS. 2A and 2B.

Generally stated, the at least one turbulence promoter 75 can be configured in different manners and can reside inside an enclosed air space that is intermediate a mouthpiece 52 (exit port) (FIG. 2A) and (downstream of) a drug compartment(s) or DCS 25 (FIG. 3). For example, the turbulence promoter 75 can be held in the airflow path 40 (FIG. 2A) and can be configured as one or more of fins, a conical, concave or projecting body (projecting in the direction of inspiratory airflow), a spiral member, a mesh, a fin oriented with its thin side in the direction of flow (FIGS. 13A, 13B), and/or a flow path geometry that can promote turbulence, and may slow the powder flow as it approaches and/or exits the inhaler 50 at the mouthpiece port 52 (FIG. 2A). The turbulence promoter 75 can facilitate deagglomeration while reducing the likelihood of inadvertently trapping any significant amount of dry powder and provides suitable inspiration resistance to thereby facilitate reliable dosing during use.

It is noted that the turbulence promoters described herein can be used with any suitable inhaler and they are not to be limited to their use with the specific inhalers described herein.

Figure 30:
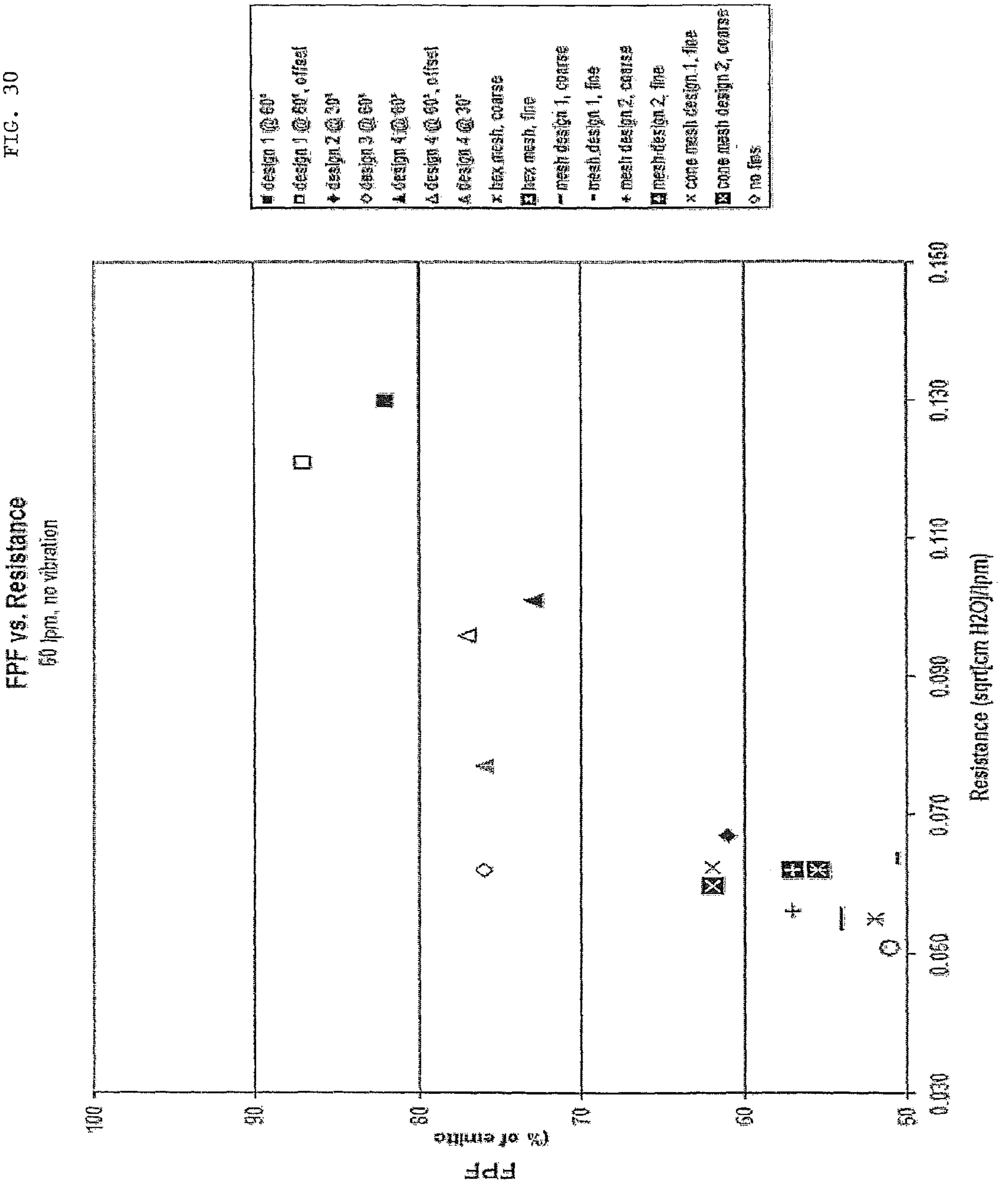
FIG. 30 is a graph of the percentage of Fine Particle Fraction ("FPF") emitted as a function of resistance.

Some embodiments of the invention employ some designs similar to those proposed or in U.S. Pat. No. 4,981,368 ("the '368 patent"), the contents of which are hereby incorporated by reference as if recited in full herein. However, the '368 patent is directed to macroflow steady state gas or liquid mixing using ramped tabs. In contrast to some of the embodiments that will be discussed below, the '368 patent is directed to cross-stream mixing and states that "a tab shape, such as a triangle, is not desired because complete revolution would not be attainable near the forward apex of the triangle" (col. 8, lines 66-69). Surprisingly, some inventors of the instant invention conceived that it might be possible to deagglomerate dry powders in transient flow inhalers if the designs could be made to inhibit trapping of particulates or granules, which is not of concern in liquid or gas mixing systems, and if inspiratory resistance could be made acceptable. The present invention is directed to deagglomeration of dry powder using transient airflow of relatively short duration and turbulence promoters such as fins and/or mesh disposed in the airpath to deagglomerate the dry powder. A graph of data regarding the FPF vs. Resistance of an exemplary dry powder drug formulation and different turbulence promoters that occlude portions of the flow path is shown in FIG. 30 and will be discussed below.

For clarity, it is noted that the exemplary flow patterns shown in the figures and described herein have not been modeled or experimentally confirmed for transient flow, but rather come from a steady state flow. However, the experiments summarized in FIG. 30 were done with transient flow (rather than steady-state). Thus, at the time of filing this patent application, it has not been confirmed that the vortex flow patterns are the same under transient flow, but it is contemplated that the turbulence levels and complex flow patterns achieved under transient flow are comparable to that achieved under steady-state flow and/or that the shapes otherwise provide the deagglomeration that results in the FPF and resistance measurements in FIG. 30. For clarity in evaluating infringement, of an inhaler regarding certain of the claim recitations directed to the particular flow patterns claimed, it is contemplated that models of steady state flow conditions may be used, although such flow patterns may exist in transient flow and it may also be possible to evaluate such claimed flow pattern recitations in an inhaler device under transient flow conditions.

Figure 2B:
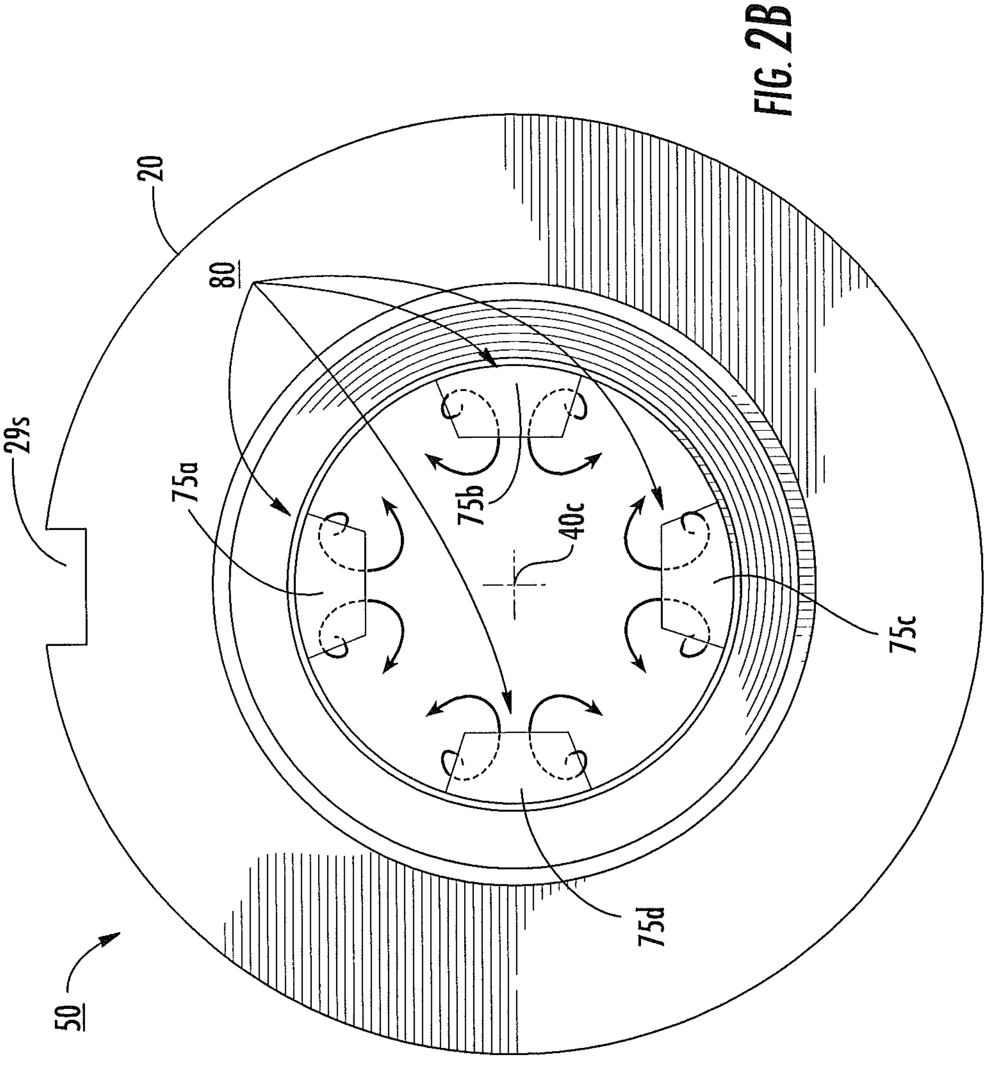
FIG. 2B is an end view of an inhaler device shown in FIG. 2A.

FIGS. 2A-2B illustrate one embodiment of an inhaler with a deagglomerating segment 51 that encloses at least one turbulence promoter 75 that includes a plurality of fins **75*f* (shown in FIG. 2B as two arrays of four fins 75*a*, 75*b*, 75*c*, 75*d*) that are angled inwardly from a bounding surface 76 in the direction of flow 40 (with the primary direction of flow or inspiration shown by the arrow) at an acute angle 77. Typically, the angle 77 is between about 10-60 degrees, more typically between about 30-60 degrees, and may be the same or different for all of the fins 75*f*. Further, more or fewer fins 75*f* and different fin configurations than those shown in FIGS. 2A and 2**B can be employed. For example, 2 fins or more, provided in even numbers (4, 6) of fins, can be used. In other embodiments, 3 fins or more, provided in odd numbers (5, 7) may be used. Combinations of odd and even numbers of fins in adjacent axially spaced arrays of fins may be used.

As shown in FIG. 2A by the linear arrows labeled "**40*u*" flow upstream of the turbulence promoter 75 (in this case fin 75*f*) is generally straight in the direction of inhalation. However, as the air and dry powder interact with the turbulence promoters 75, a turbulence flow pattern is created. In some embodiments, the flow pattern can include vortices 40*v* (indicated by the rotation arrows in FIG. 2**A). For clarity, only an exemplary flow pattern with respect to the fins aligned on the bottom of the inhaler flow path is illustrated.

Figure 2C:
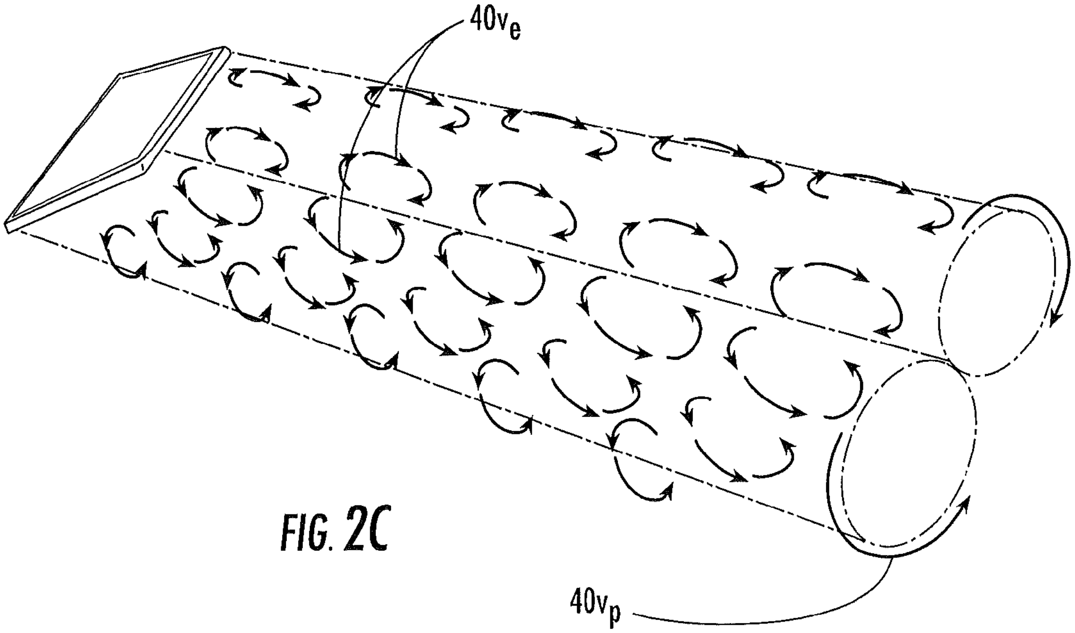
FIG. 2C is a side perspective view of an exemplary flow pattern that can be generated by a fin (having sharp points and long edges) according to embodiments of the present invention.

FIG. 2C illustrates a side view of a flow pattern that includes different types of flow vortices, one flow vortex type **40*vp* having an axis of rotation in the axial direction (the tip or point induced vortices) and the other type being a shedding vortex 40*ve*** (also can be described as a ripple or wave vortex type) with an axis of rotation that is generally orthogonal to the flow direction (the long edge induced vortices). A more complete description of some steady state flow patterns can be found at Chemineer Mixers and Agitators which proposes a tab geometry for HEV Static Mixers, see the URL Chemineer.com for a description of a static mixer (known as the KENICS® static HEV mixer that uses tabs similar to that described with respect to the '368 patent).

Vortices 40*v* can be generated by each fin 75*f* as the air and dry powder travel in the inspiratory direction of a user. FIG. 2B illustrates an exemplary flow pattern with each fin 75*a*-75*d* having two sharp point or tip portions disposed at the loci where two long edge portions meet. The points can generate paired vortices, with each vortex rotating in an opposite direction with respect to the adjacent paired vortex. Other fin configurations will be discussed below. Different fin configurations can be used to occlude more or less of the cross-sectional space, some leaving an open center space in the flow path 40*c* some occluding the center space (when viewed downstream of the fins) as will be discussed below.

In some embodiments, as shown in FIG. 3, two or more array(s) of fins $80_1$, $80_2$ can be used in at least two different axially spaced apart locations in the inspiratory flow path 40. The term "array" refers to a set pf fins 75*f* that are disposed at the same axial location, i.e., they start from substantially the same axial bounding location. The array of fins may also be configured so that each respective fin extends generally coextensively (with substantially the same length) in the direction of flow, but are spaced apart about the perimeter of the interior surface or wall. Thus, as shown in FIG. 2B, each array 80 can have four fins 75*a*, 75*b*, 75*c*, 75*d* equally spaced about a perimeter inner wall of the flow path 40. Each array 80 can have the same or different numbers of fins from another array. In some embodiments, each array of fins can have substantially the same angle of inclination in the flow direction (also known as the streamwise direction) and the fins 75 may be equally spaced apart about an inner perimeter of the inspiratory flow path in the deagglomerating segment 51 of the inhaler 50. In some other embodiments, each or some of the array of fins (or fins in a respective array) can have a different angle of inclination in the flow direction and the fins may be unequally spaced apart about an inner perimeter of the inspiratory flow path in the deagglomerating segment 51 of the inhaler 50. Combinations of the above configurations may also be used.

FIGS. 2A and 3 also illustrate that a turbulence promoter 75 can be disposed in the flow path 40 downstream of at least one drug compartment 25, the dry powder input, or a DCS input.

Figures 16A, 16B, 16C, 16D, 16E:
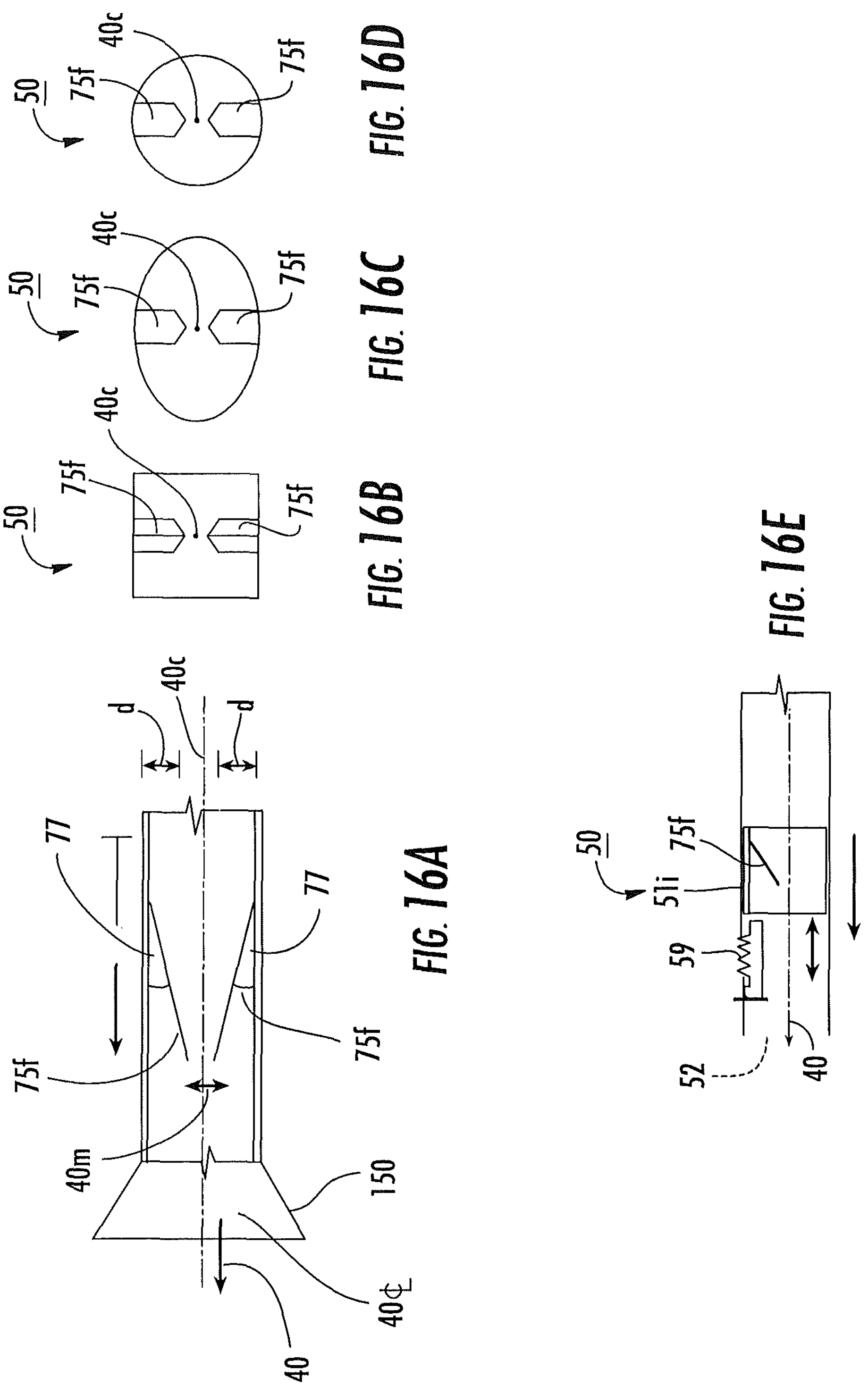
FIG. 16A is a side axial partial section view of a schematic illustration of a portion of an inspiratory flow path of an inhaler with fins according to embodiments of the present invention.
FIGS. 16B-16D are an end views of exemplary alternative geometric shapes of the flow path of the inhaler shown in FIG. 16A according to embodiments of the present invention.
FIG. 16E is a schematic illustration of a side view of a portion of an inhaler flow path according to embodiments of the present invention.

The inspiratory flow path 40 (at least about the deagglomerating segment 51) can have a circular cross section but may also have other shapes, such as, but not limited to, rectangular, square, elliptical, oval, curvilinear, triangular, and polygonal. FIGS. 16B-16D illustrate exemplary shapes enclosing the flow path center 40*c*.

The turbulence promoter(s) 75 can be integrally molded to the inner surface of the inspiratory flow path 40 or may be provided as an insert or discrete attached member. The molded version may be injection molded. In the embodiment shown in FIGS. 2A and 3, the turbulence promoter 75 is an insert 51*i* that can be frictionally and/or adhesively attached to the inner wall of the inhaler 50. The turbulence promoter 75 can comprise a metallic material or other pharmaceutically compatible material, such as a resin, a ceramic, and/or a polymer material or a combination of materials. In some embodiments, the turbulence promoter 75 can comprise a malleable metal such as stainless steel that is able to be formed into a desired shape and retain that shape during operation. The insert and/or inhaler can be sterilized and packaged for medicinal use and distribution according to embodiments of the present invention.

FIG. 3 illustrates that the turbulence promoter 75 can have a first length $L_1$ and may be used with a tubular inhaler having an inner member 30 with a second length $L_2$, and an outer member 20 that can have a third length $L_3$. The inhaler 50 can position a drug compartment 25 downstream of the deagglomerating segment 51 and the drug compartment or DCS can have a fourth length $L_4$. The outer member length $L_3$ can be the longest, followed by the inner member length $L_2$. FIG. 3 also illustrates that the inhaler 50 can have a collar 29 with a slot 29*s* on an outer surface of the outer member 20 that is configured to index the outer member 20 in a desired orientation in the inhaler 50.

FIG. 3 also illustrates that the inhaler 50 can include a drug filling port 24 and an active vibrating or flexing member 26 that is in communication with the dry powder holding compartment or DCS and can vibrate the powder to assist in the flowability and release from the inhaler 50.

FIGS. 4-9 illustrate exemplary alternate shapes for the fin 75*f*, some having more than two points (designated generally by 175*p*, 275*p* et seq.) and edges (designated generally by 175*e*, 275*e* et seq.) that reside in the flow stream 40 a distance away from the bounding surface. The fins can include long and/or short edges. The term "long" means that the edge defines a side of a fin. For ease of discussion, the term "fin" will be discussed generally herein as represented by reference feature 75*f* and this reference is meant to include all fin configurations, including those shown and described. However, for discussions with respect to the fin shapes shown in FIGS. 4-9, a numerical prefix will be used to indicate the particular fin configuration (175*f*, 275*f*, 375*f*, etc. . . . ).

The shapes of the fins 75*f* are shown flat in FIGS. 4-9 for ease of discussion and in an exemplary fabrication configuration. As also shown, the fins 75*f* can be cutout, stamped or otherwise formed into a planar sheet that can be configured to hold at least one array of fins 80. The fins 75*f* can be malleably angled into the desired orientation and the planar support substrate can be formed into the shape of the wall(s) defining the deagglomeration segment 51 (FIG. 2A) of the flow path 40. However, the fins 75*f* may be individually formed and attached to the wall or bounding surface (directly or indirectly). The attachment can be via any suitable means such as welding (metal or ultrasonic), brazing, adhesive, or otherwise to affix the fins) into position. In some embodiments, the fins 75*f* can be molded as an insert or integrally formed into the wall of the flow path 40.

Figure 4:
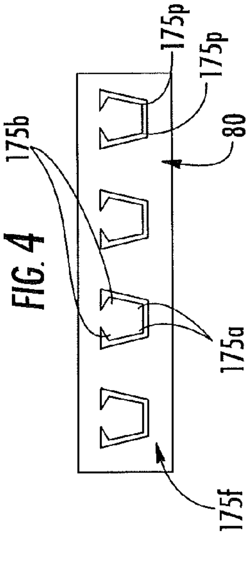
FIGS. 4-9 are top views of examples of fin shapes according to embodiments of the present invention.
Figure 5:
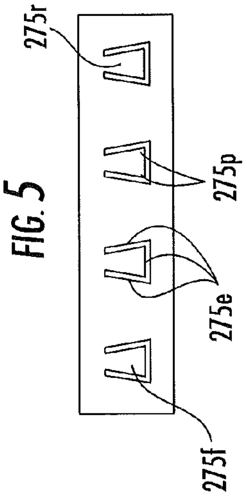

FIG. 4 illustrates a "shape 1" fin 175*f* with two points 175*p* and three long edges 175*e* including two forward points 175*a*. As shown, the shape may include two rearward points 175*b* that allow the fin to bend into a desired angle. In position in the air path, the rearward points 175*b* reside substantially adjacent the bounding surface, away from the primary portion of the airstream in the airflow path and, hence, these rear "points" do not typically substantially interact with the airflow/powder. FIG. 5 illustrates a "shape 2" fin 275*f* with two forward points 275*p* at opposing forward corners of the fin 275*f* with a width that tapers to a more narrow rearward portion 275*r*. The shape includes three long edges 275*e*.

Figure 6:
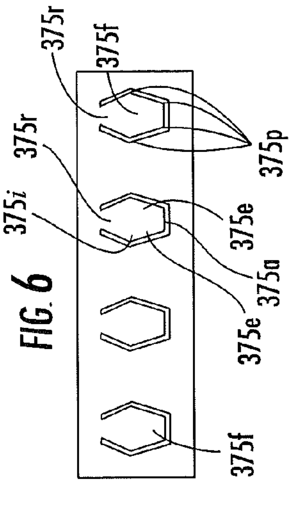

FIG. 6 illustrates a "shape 3" fin 375*f* with four points 375*p*. The fin body 375*b* has a perimeter with a first width at a forward portion 375*a* that tapers out to a second wider width proximate the intermediate edges 375*i*, then tapers into a more narrow rearward portion 375*r*. This shape has three long edges 375*e* that can reside in the flow stream.

Figure 7:
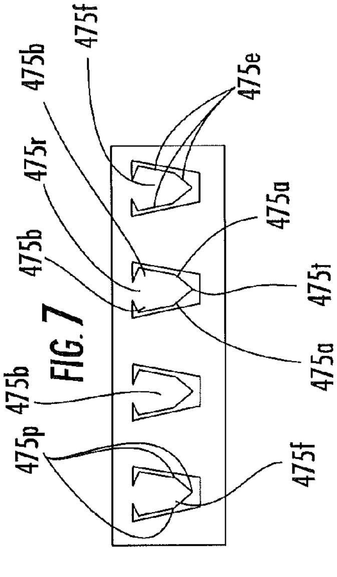

FIG. 7 illustrates a "shape 4" fin **475*f* with three points 475*p*. This fin body 475*b* has a tip 475*t* that tapers out into two forward edges 475*a*. As for the shape shown in FIG. 4, the fin 475*f* tapers out to form two rearward edges 475*b* proximate the rearward portion 475*r* of the fin. In position, the rearward edges 475*b* are proximate the bounding surface in the direction of the airflow path and substantially do not interact with the airflow in the inspiratory airflow path. This shape has four long edges 475*e*, adjacent ones of which meet at a point 475*p***.

Figure 8:
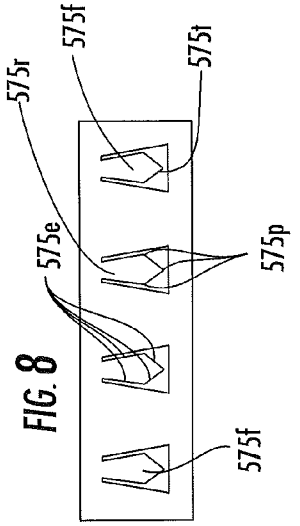
Figure 9:
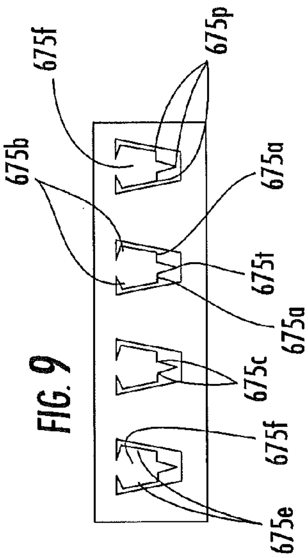

FIG. 8 illustrates a "shape 5" fin **575*f* with three points 575*p*, one of which is a forward tip 575*t* that tapers out into two intermediately positioned edges 575*i*. This shape has four long edges 575*e*. FIG. 9 illustrates a "shape 6" fin 675*f* with multiple points 675*p*, including a forward tip 675*t* and two forward points 675*a*. Again, similar to the shapes shown in FIGS. 4 and 7, this fin tapers out to two rearward points 675*b*. In position, the rearward points 675*b* reside proximate the bounding surface. The tip 675*t* merges into forward inner corners 675*c* (spaced inward from outer edge points 675*a*) that may also promote turbulence. This shape has four long edges 675*e* and an additional two edges that connect the tip 675*t*** to the outermost edges (and some edges are shorter than others).

Figure 10A:
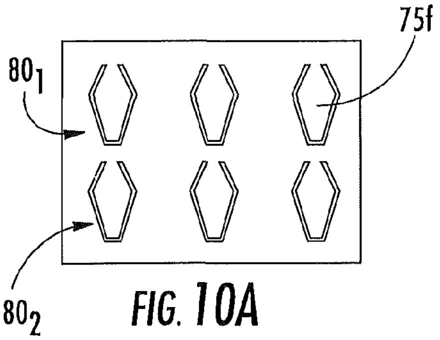
FIGS. 10A and 10B are top views of shapes for a plurality of fins that can be aligned (front to back) in position and may be sized and configured according to embodiments of the present invention.
Figure 10B:
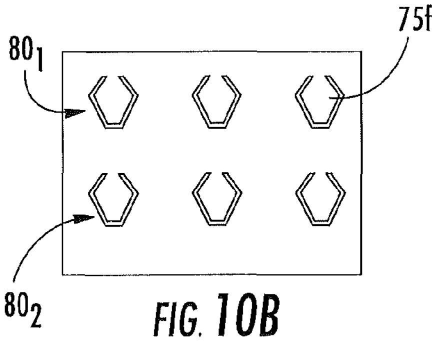

FIGS. 10A and 10B illustrate fins **75*f* having a shape similar to that shown in FIG. 6 (375). The fins 75*f* shown in FIG. 10A are configured so that in position, they have an angle of inclination of about 30 degrees with respect to the bounding surface. The fins 75*f* in FIG. 10**B are configured to have an angle of inclination of about 60 degrees with respect to the bounding surface when in position.

The fins **75*f* in FIG. 10**B have a shorter length as they have a greater angle and reach their desired position in the airflow path with less length.

Figure 10C:
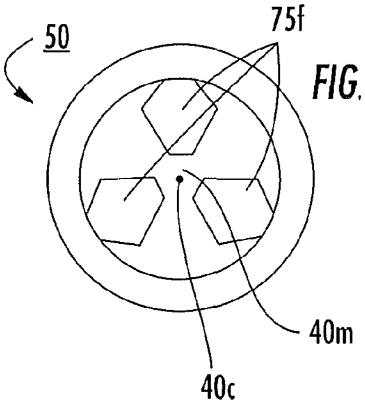
FIG. 10C is an end view of a fin insert with the fins aligned and held in an inspiratory flow path according to embodiments to the present invention.

The fins **75*f* shown in FIG. 10A can reach the same spatial location in the flow path, but over a greater axial distance. FIG. 10C illustrates an end view of the inhaler 50 using either the fins shown in FIG. 10A or 10B. FIGS. 10A and 10B also show the fins 75*f* can be arranged in two aligned arrays, $\mathbf{80}_1$, $\mathbf{80}_2$ of three fins 75*f*** each.

Figure 11A:
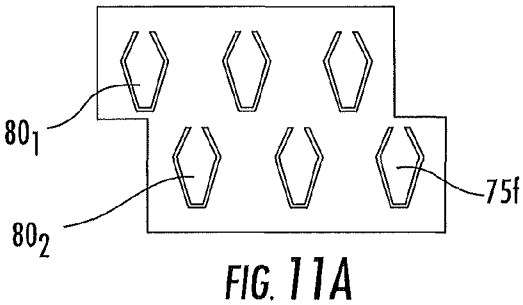
FIGS. 11A and 11B are top views of fin shapes with a plurality of fins that can be offset (front to back) in position and may be sized and configured according to embodiments of the present invention.
Figure 11B:
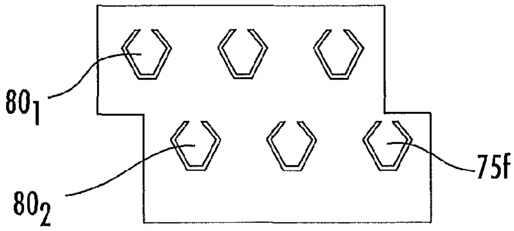
Figure 11C:
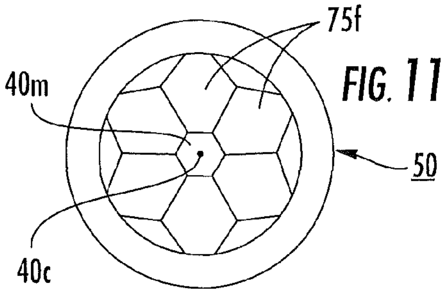
FIG. 11C is an end view of a fin configuration with the fins offset and held in an inspiratory flow path according to embodiments to the present invention.

FIGS. 11A and 11B illustrates fins corresponding to those shown in FIGS. 10A and 10B, but with the fins offset or not in axial alignment. That is, the fins in the first array $\mathbf{80}_1$ can be rotated with respect to the fins in the second array $\mathbf{80}_2$. FIG. 11C illustrates an end view of the fins **75*f* installed in the offset configurations of FIG. 11A or 11**B.

As shown in both FIGS. 10C and 11C, the fins **75*f* can be configured, as viewed from the end, to occupy at least about a major portion, and typically greater than a major portion, of the cross-sectional area of the flow path 40. In some embodiments (viewed from the end or in cross section downstream of the fins), the fins can be configured to leave an open center space 40*m* (around center of the flow path 40*c*). In particular embodiments, the cross sectional area of the flow path may be about 200 $mm^2$ or less, typically about 100 $mm^2$ or less and the center free space 40*m* can have cross-sectional width or distance that is between about 10-70%, typically between about 20-60%, of the cross sectional width of the flow path thereat. In some embodiments, the open space 40*m*** may have an area that can be about 30 $mm^2$ or less, and may be between about 2-15 $mm^2$.

In particular embodiments, for a deagglomeration segment 51 of an airflow path 40 having a cross-sectional width "W" and length "L", the fins **75*f* can extend from a respective bounding surface (such as from opposing sides of a wall) and occupy about 25% each (total about 50%) of the W and/or L, leaving the center space 40*m*** having about 50% of the distance L and/or W.

In some embodiments, the inhaler 50 has a tubular shape with respect to the deagglomerating segment 51, with a cross-sectional diameter of about 10 mm, typically about 8 mm or about 6 mm. The open center space **40*m* may have a width (measured side to side and/or top to bottom) of between about 1-6 mm. For example, a flow path of about 6 mm diameter can have an open center space 40*m* of between about 2-4 mm, a flow path of about 8 mm diameter can have a open center space 40*m* of between about 2-5 mm, and a flow path of about 10 mm diameter can have an open space 40*m* of between about 3-6 mm. The flow path 40 can have different cross-sectional widths at different portions of the deagglomerating segment 51** or may have the same width and area along the length thereof.

As shown in FIG. 11C, the fins **75*f* can converge to form a substantially hexagonal center opening shape 40*m* when viewed from the end or in transverse cross-section downstream of the deagglomerating segment 51 (FIG. 2**A).

In other embodiments, the fins **75*f*** can provide a totally occluded center space (when viewed from the end) as a series of fins can be arranged to leave no open center space, one or more fins can be sized and configured to extend greater than a major distance across the span of the flow path. The bounds of the fins can visually meet to close the center or bounds of one or more of the fins can extend a further distance to overlap with the bounds of another.

For example, as shown in FIGS. 12A-12E, the fins **75*f* can be configured as a plurality of single substantially triangular shaped fins 775*f* spaced axially, apart and sized to define a closed center space when viewed from the end. As with the other fins 75*f*, the fins 775*f* can be oriented at an acute angle to extend into the flow path from a bounding surface. Each fin 775*f* can have the same or a different angle of orientation. A single fin 775*f* can be located at a respective axial location and the next adjacent fin can be circumferentially spaced apart at a different axial location so that, when viewed from the end as shown, the center space is substantially closed. Thus, the fins 775*f*** are configured with the fin boundaries that meet or overlap to provide a closed end view with an increased "effective area" (the area that appears to be blocked when looking straight down the airpath). Other occluded fin design shapes may also be used.

Figure 12A:
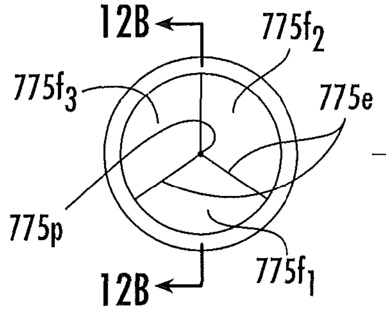
FIG. 12A is an end view of another fin configuration.
Figure 12B:
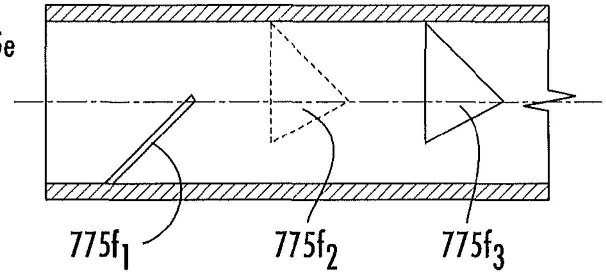
FIG. 12B is a side section view taken along line 12B-12B of FIG. 12A.
Figure 12C:
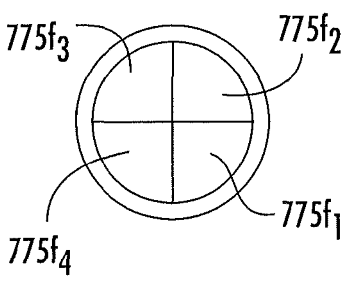
FIGS. 12C-12E are end views of alternate fin configurations similar to that shown in FIG. 12A.
Figure 12D:
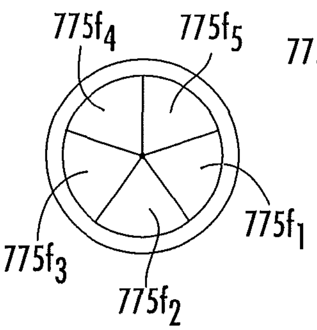
Figure 12E:
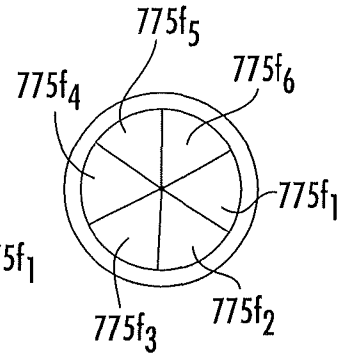

FIG. 12B illustrates a side section view of the embodiment shown in FIG. 12A with three fins **755*f* ($\mathbf{775}f_1$-$\mathbf{775}f_3$), each having at least one point 775*p* and two long edges 775*e* that can extend from a different portion of the air path wall from different axially spaced apart locations. FIGS. 12C-12E illustrate that greater numbers of fins 775*f*** can be used.

Figure 13A:
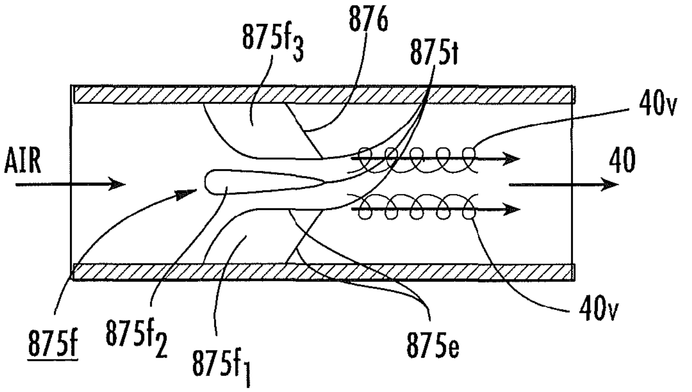
FIG. 13A is a side section view of yet another deagglomerating segment of an inhaler according to embodiments of the present invention.
Figure 13B:
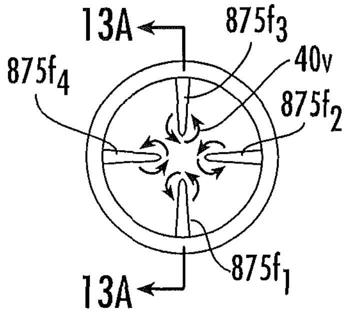
FIG. 13B is a front view of the configuration shown in FIG. 13A.

FIGS. 13A and 13B illustrate yet another fin **75*f* configuration. In this embodiment, the fins 875*f* (designated individually as $\mathbf{875}f_1$-$\mathbf{875}f_4$) are turned relative to the fin configurations discussed above, with the minor (thin) dimension of the fin body 875*f* facing downstream with the axial cross section being elongate. In this embodiment, the fin 875*f* is not required to angle inwardly from the bounding surface. Rather, the fin body can be configured to define a relatively thin, typically less than 10% of its length, front profile (FIG. 13B) with a longer side profile (FIG. 13A). FIG. 13B illustrates that four equally spaced apart fins 875*f*** may be used, but lesser and greater numbers may also be used and the spacing and angles may differ from that shown.

As shown in FIG. 13A, each fin **875*f* can have a curved upstream portion with the body first rising then tapering down to merge into a trailing edge that forms a wing tip 875*t*, similar to an airplane wingtip, at a forwardmost (downstream location). The wingtip 875*t* can reside proximate a generally medial portion of the flow path. The tip 875*t* may generate point or tip induced flow vortices 40***v* with their respective axis of rotation being in the axial flow direction as shown schematically in FIG. 13A. Although shown as configured in a first array of fins in FIG. 13B, the fins 875*f* may be used as more than one set or array of fins, may be used as a single fin or axially spaced singles or multiples of fins (not shown). Also as shown, the fins 875*f* can be configured to extend across a sub-portion (less than the entire width) of the cross-sectional width or diameter of the air path at their respective axial location. Typically, a respective fin 875*f* can extend across about 20-80% of the air path.

In some embodiments using arrays of fins, opposing pairs of fins in the array can be configured to extend cumulative between about 25-40% of the cross-sectional width so that an open medial space 40*m* remains. In other embodiments, fins in certain fin arrays can be sized to define a closed center space 40*m* therebetween (when viewed from the end).

Unlike the '368 patent discussed above, the fins 75*f* can be spaced and configured so that the vortices from points interfere with each other and/or so that adjacent ones do not form full vortices. That is because in the instant invention the fins 75*f* are directed to facilitate deagglomeration rather than to mix the dry powder. It is contemplated that the fin 75*f* (or arrays of fins) can be configured to be relatively closely axially spaced, such that the forward end of the upstream fin can terminate as the rearward end of the downstream fin starts to angle in from the bounding surface. In some embodiments, adjacent arrays of fins can be spaced apart a distance of between about 1-12 mm, and may be typically spaced at about the same distance as the cross sectional width (diameter) of the air path.

FIG. 14 is a schematic illustration of a design of proportion where C is the overall distance, and A is to B as B is to C (a 1.618 ratio). The proportion is also known as the Fibonacci numbers or series and is used in many man-made designs and is also naturally occurring in nature. See, e.g., the URL at goldennumber.net.

Some embodiments of the present invention employ the proportion (A is to B as B is to C) as shown in FIG. 14 to design a fin configuration useable for inhalers. The dimension "C" can represent a cross-sectional area of the deagglomerating section 51 (FIG. 2A) of the inhaler flow path 40. The dimension "A" can represent the total surface area of the fins 75*f* at a first location (calculated using the shape in the end view). The remaining surface area for (turbulent) air flow can be dimension "B", which can be described as the golden cut of the area of the airpath. The fins 75*f* can have high energy areas located at the forwardmost edges at a diameter "A" location in the flow path 40. The fins 75*f* may be equidistantly spaced around the circumference at a common angle (such as at about 45 degrees or other acute angle). The fins 75*f* can be repeated at a distance "C" downstream of the first array of fins (FIG. 15B). The fins 75*f* in the second array $\mathbf{80}_2$ can be rotated 60 degrees in relation to the first array $\mathbf{80}_1$ (when viewed from the end). As noted above, other rotations of alignment may be used and/or the fins can be aligned. Rotation of the fins does not change the high-energy area 75*h* created by the fin edges. As an example of sizing, given an inhaler having a diameter of 6 mm, the cross-sectional area is 28.274 $mm^2$ ("C"). The total surface area of three fins at array $\mathbf{80}_1$ (FIG. 15B) is 10.799 mm2 ("A"). The remaining surface area is 17.475 $mm^2$ ("B"). The second array $\mathbf{80}_1$ can be positioned C (28.274 mm) downstream of the first $\mathbf{80}_1$. The axial spacing distance can be measured from the beginning of one set or array of fins to the next set or array of fins. Where the angles of the fins are the same, the measurement can also be from end of the first set or array of fins to the end of the next set.

FIG. 16A illustrates that the inhaler 50 can include a diffuser 150 downstream of the fins 75*f*. The diffuser 150 may expand the flow path 40 about 5-20 degrees, typically about 7-9 degrees, in the direction of flow. In other embodiments, a diffuser is not required and the airflow path may be shortened to be less than about 1 inch, sometimes less than about 0.75 inches.

As is also shown, the fins 75*f* can have an angle 77 and a length "L" that directs the fins 75*f* to taper into the flow path to reside at a desired location in the flow path 40. The fins 75*f* may extend inwardly a distance "d" from the bounding surface toward the center of the flow path 40*c*. As noted above, the distance d may be sufficient to cause the fins to occupy greater than a major portion of the flow path cross-sectional area. The distance L is dependent on the angle 77 selected and/or the distance "d" into the airpath the fin is desired to reach. Thus, for example, an "L" of a fin (single) or a fin in a fin array can result from a selection of "d" and the angle of orientation desired.

FIGS. 16B-16D illustrate that the deagglomerating segment 51 of the inhaler 50 may have a non-circular flow path 40 in some embodiments.

FIG. 16E illustrates that the fins 75*f* may be configured to translate during operation. That is, typically, the fins 75*f* are static in the airflow path 40. However, the fins 75*f* may be configured to flap or flex generally orthogonal to the primary flow direction (not shown) in response to inspiratory pressure. As shown, the fins 75*f* can be mounted on a collar or insert 51*i* that translates forward in response to inspiratory pressure (as indicated by the arrow). The insert 51*i* may also be floating so as to be able to rotate captured in the inhaler flow path as well as (or alternatively) translate forward. The insert 51*i* can be biased to return to a home position in the absence of inspiratory pressure. The biasing can be formed using any suitable mechanical means, such as a spring or resilient member 59 that pushes the insert 51*i* back to a non-use position.

FIGS. 17-25 (all 3-D views) illustrate that instead of fins 75*f*, the turbulence promoters 75 can be formed as a mesh body 1000. Each can be sized and shaped to fit the desired inhaler size and shape. For ease of discussion, the mesh bodies will be referred to generally by the reference number 1000. Each different mesh body 1000 having a shape corresponding to those shown in FIGS. 17-25, will be described as a specific reference number 1100-1109, respectively. The mesh body 1000 can have a planar 2-dimensional shape or may have a 3-dimensional shape. The embodiments shown in FIGS. 17-21 are directed to the 2-dimensional flat shapes. FIGS. 22-26 are directed to some exemplary 3-dimensional shapes. In some embodiments, the flat mesh body 1000 can be oriented in the flow path 40 to angle axially forward or rearward and/or side-to-side. In other embodiments the flat mesh body 1000 may be positioned substantially orthogonal to the direction of flow. Combinations of the mesh bodies as well as fins 75*f* may also be used (not shown). In other embodiments, the mesh body can be configured as a 3-D shape that projects forward in the air flow path (the shape can be generally convex) (not shown).

As shown, the mesh bodies 1000 can have mesh configurations that have internal and/or external points 1000*p* that can create flow turbulence. In some embodiments, the mesh configurations may be configured to generate flow vortices, with points 1000*p* and long edges 1000*e* similar to those shown with respect to the fins 75*f* described above or may configured to facilitate deagglomeration in other manners (impaction, turbulence, etc.). The mesh 1000 may be configured to extend across all or a portion of the flow path 40.

Figure 17:
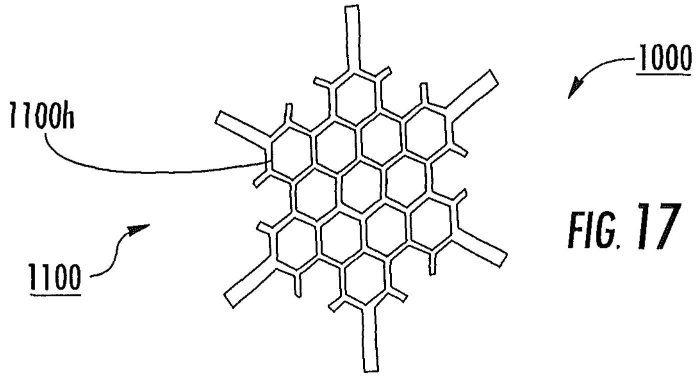
FIGS. 17-22 are top views of exemplary generally planar (two-dimensional) mesh configurations that provide fins that deagglomerate dry powder according to embodiments of the present invention.
Figure 18:
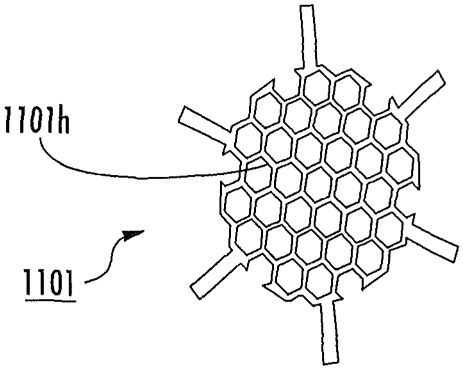
Figure 19:
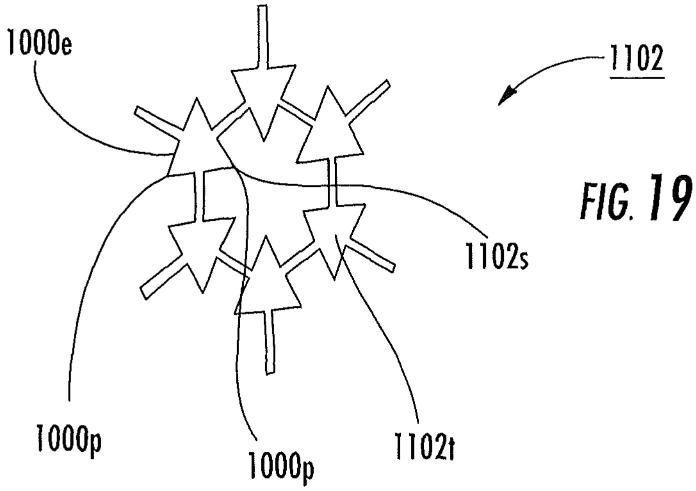
Figure 20:
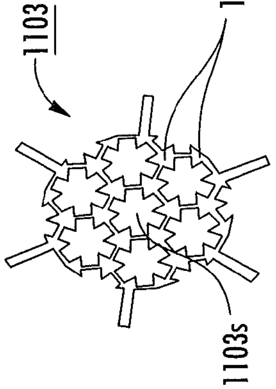

FIG. 17 illustrates a coarse hexagonal and flat mesh 1100. The coarse mesh typically has less than about 4 open hexagonal cells 1100*h* per about 10 $mm^2$. FIG. 18 illustrates a fine hexagonal flat mesh 1101 with greater numbers of cells 1101*h* per square mm than that of the coarse mesh (typically about 5 cells or greater per 10 $mm^2$ but sufficiently open not to unduly trap dry powder in the inhaler during inspiration). FIG. 19 illustrates a flat triangular mesh 1102. The triangles 1102*t* are shown as closed or solid bodies, but may be configured as open cells in other embodiments (not shown). FIG. 20 illustrates a fine flat triangular mesh 1103 with increased numbers (and smaller size) triangles 1103*t* relative to the coarse mesh 1102. The coarse mesh and/or fine mesh 1103, 1102 may be configured to define an open central space 1102*s*, 1103*s*.

Figure 21:
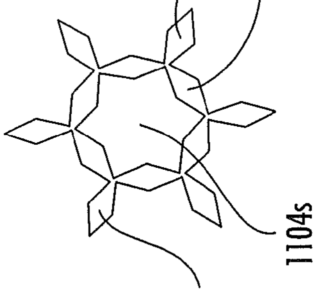
Figure 22:
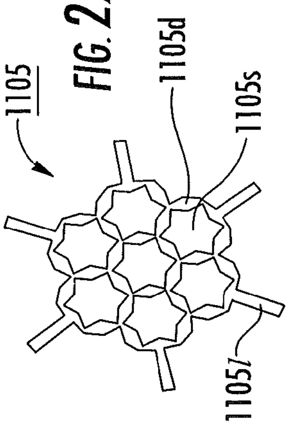

FIG. 21 illustrates a diamond coarse flat mesh 1104 and FIG. 22 illustrates a fine diamond flat mesh 1105 that can be arranged to substantially define star-shaped open cells 1105*s*. The coarse diamond mesh 1104 may be arranged so that the diamond shapes 1104*d* are clustered about a perimeter and leave the center open and in a substantially star-like shape 1104*s*. The legs 1104*l* connecting the mesh to the wall or bounding surface may also have the diamond shape (FIG. 21) but may be shaped otherwise (FIG. 22). All or some of the diamond shapes 1104*d*, 1105*d* may be open rather than closed as shown.

FIGS. 23-26 illustrate that the mesh bodies 1000 can have 3-D shapes that extend a distance along the inspiratory flow path 40. The exemplary 3-D shapes may be generally conical whereby the mesh 1000 tapers from a wider configuration at a start location to a narrower configuration at a second location downstream of the first location. The 3-D shapes may converge in the downstream location to terminate at a tip (open or closed) or form a frustoconical shape.

Figure 23:
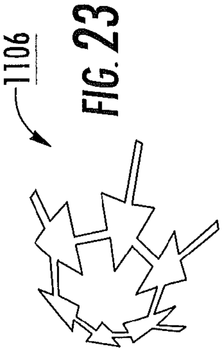
FIGS. 23-26 are perspective views of three-dimensional mesh configurations that provide fins that deagglomerate dry powder according to embodiments of the present invention.
Figure 24:
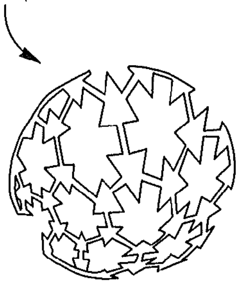
Figure 25:
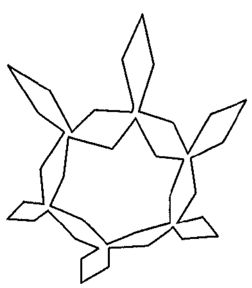
Figure 26:
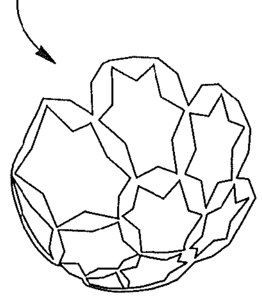

FIG. 23 illustrates a coarse triangle mesh 1106 similar to that shown in FIG. 19, but shaped to have the triangles 1106*t* incline and converge to a medial portion of the airflow path. FIG. 24 illustrates a fine triangle mesh having a cone-like shape 1107. FIG. 25 illustrates a cone-like, coarse, diamond shaped mesh 1108. FIG. 26 illustrates a cone-like fine diamond mesh 1109.

Figures 27A, 27B, 27C, 27D:
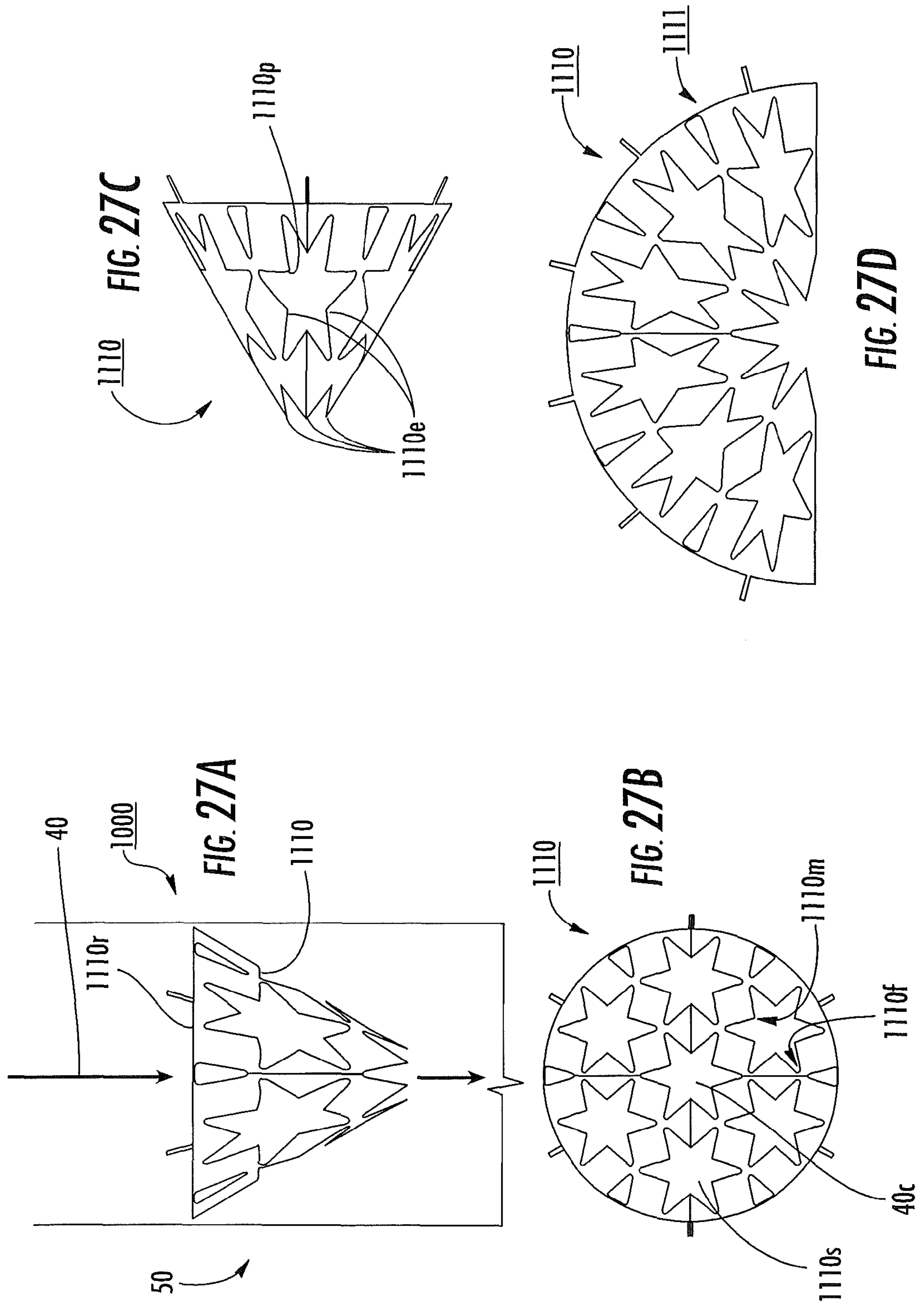
FIG. 27A is a top view of an exemplary mesh that can facilitate deagglomeration according to embodiments of the present invention.
FIG. 27B is a front view of the mesh shown in FIG. 27A.
FIG. 27C is a side view of the mesh shown in FIG. 27A.
FIG. 27D is a top view of a mesh configuration shown in FIG. 27A illustrated as an unrolled planar member according to some embodiments of the present invention.

FIGS. 27A-27D illustrate yet another 3-D shaped mesh body 1000, which includes a mesh 1110 of edges and points including relatively sharp male points 1110*m* and female points 1110*f*. The mesh 1110 may comprise open cells 1100*s* having 6-point and/or 6-leg star shapes 1110*s*. The female points 1110*f* may have a slightly rounded edge, such as about 0.05 mm fillets. The diameter of the rearward portion 1110*r* can be sized to reside inside and correspond to the size of the flow path (i.e., for a 6 mm diameter flow path, the diameter may be about 5.9 mm). FIG. 27B is a front view of the conical mesh body 1110.

FIG. 27C illustrates a side view of the conical shaped body 1110. In operation the dry powder and air flow through the star shapes 1110*s*, which induces turbulence, and may induce a flow pattern with vortices due to the edges 1110*e* and or points 1110*p* residing in the flow path 40 to facilitate deagglomeration. This configuration may promote deagglomeration while inhibiting undue trapping.

FIG. 27D illustrates that the 3-D shaped mesh body 1110 may be formed from a flat surface 1111 that may be photochemically etched to form the cells or star or other shapes in the mesh. Photochemical processing is well-known. See the Url at fotofab.com for additional description. The mesh can then be rolled to provide the conical body. The mesh can be formed in the flat surface 1111 via other means, such as, but not limited to, stamping and the like.

For both mesh and fin configurations, the material and configuration should be cleanable to suitable standards. In some embodiments, the material maybe selected so as to be heat resistant or compatible with irradiation sterilization procedures because, in use, the inhaler and/or mesh may be exposed to sterilization procedures. The spiral, mesh and/or fin deagglomeration member(s) can be configured so as to be relatively easily washed or rinsed in situ or as a removable component by a user at certain times during a life cycle.

Figure 28D:
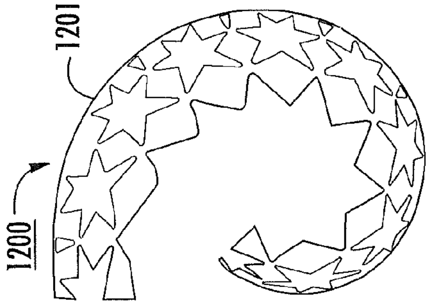
FIG. 28D is a top view of an unrolled surface that can be rolled to form the spiral mesh shown in FIG. 28A according to embodiments of the present invention.
Figure 28C:
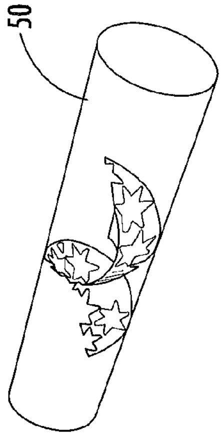
FIG. 28C is a side perspective view of the mesh shown in FIG. 28A bounded by an interior wall or member of an inhaler airflow path according to embodiments of the present invention.
Figure 28E:
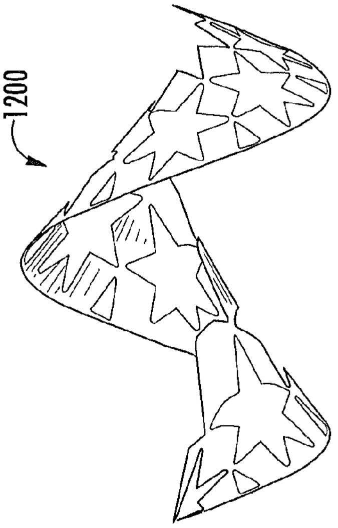
FIG. 28E is a side view of the mesh configuration shown in FIG. 28A.
Figure 28A:
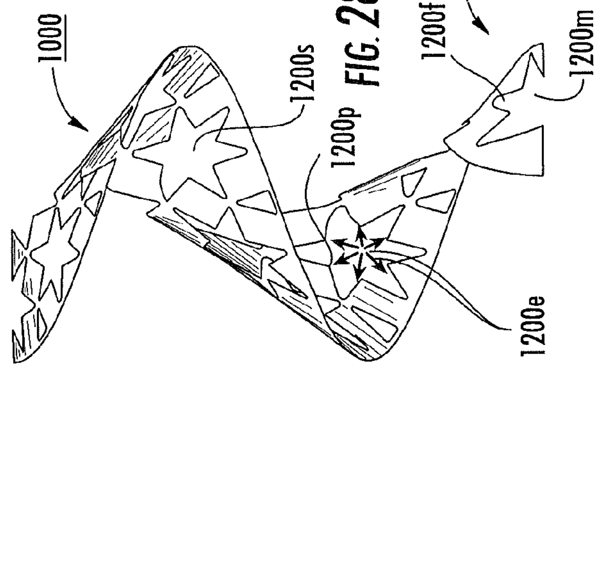
FIG. 28A is a top view of a three-dimensional spiral mesh configuration according to yet other embodiments of the present invention.
Figure 28B:
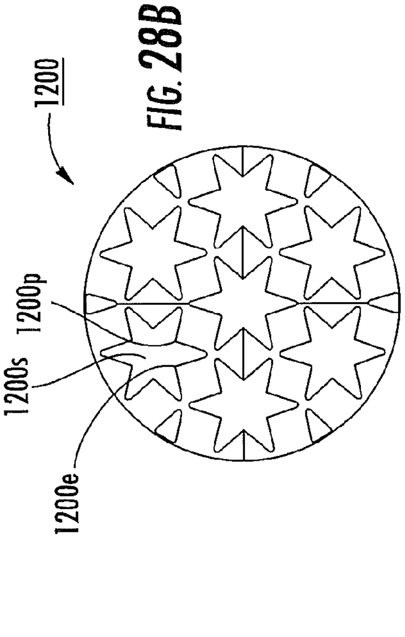
FIG. 28B is a front view of the mesh configuration shown in FIG. 28A.

FIGS. 28A-28E illustrate yet another mesh body 1000 according to embodiments of the present invention. In this embodiment, the mesh 1200 has a spiral shape. However, when viewed from the front as shown in FIG. 28B, a mesh configuration similar to that shown in FIG. 27B is shown. The mesh 1200 can have male and female edges 1200*m*, 1200*f* as described with respect to the embodiment shown in FIGS. 27A-27D. The spiral shape mesh 1200 may provide sufficient turbulence that facilitates deagglomeration in a manner that inhibits anything but de minimis trapping of the dry powder and suitable FPF and resistance. The mesh body 1200 can be configured to turn, scroll, twist, coil or otherwise spiral at least once along its length between bounding surfaces as shown in FIG. 28C. FIG. 28E illustrates a side view of the mesh body, unconstrained by the shape of the bounding surface shown in FIG. 28C. As before, as shown in FIG. 28D, the mesh 1200 can be formed into a substrate 1201 that is shapeable, such as by using a photo-resist or etchable developable surface or material.

Figure 29A:
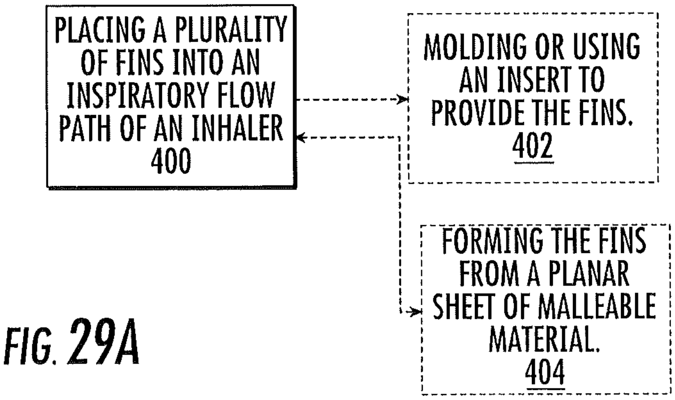
FIGS. 29A and 29B are flow charts of exemplary operations that can be used to fabricate inhaler components that can deagglomerate dry powder according to embodiments of the present invention.
Figure 29B:
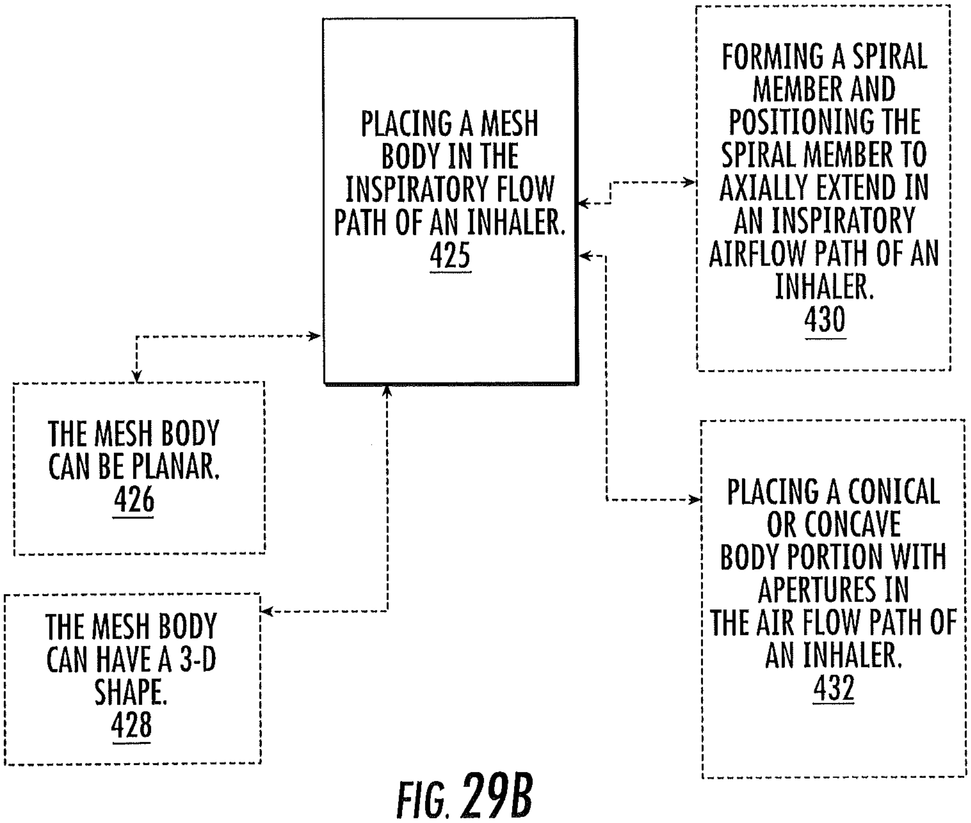

FIGS. 29A and 29B illustrate operations that can be used to fabricate inhalers according to embodiments of the present invention. A plurality of fins can be placed into an inspiratory flow path of an inhaler (block 400, FIG. 29A). An insert can be molded or used to provide the fins (block 402). The fins can be formed from a planar sheet of malleable material that is sufficiently structurally rigid to be able to hold the desired angled operational configuration (block 404).

FIG. 29B is directed to a mesh body. The mesh body is positioned in the inspiratory airflow path of an inhaler (block 425). The mesh body can be planar (block 426) or have a 3-D shape (block 428). The mesh body can be a conical and/or convex body with a generally open (or in other embodiments, closed) medial forward portion in the airflow path of the inhaler (block 430). The mesh body can be disposed in the inhaler as a spiraling member (block 432). The mesh pattern may be formed by photochemical etching.

In some embodiments, the mouthpiece port 52 (FIG. 2A) and an air inlet port (not shown) may be spaced apart about a distance of between about 12-127 mm (about 0.5-5 inches). The inhaler may have a relatively short airpath, such as between about 12-25.4 mm or a longer airpath, and typically between about 50-127 mm (about 2-5 inches). The shorter airpath can be defined to include a short tubular airpath extending proximate a drug entry location proximate the deagglomerating segment 51 and a short upstream portion that merges into the inhaler mouthpiece (not shown). The longer airpath may extend across a major portion or substantially all of a width or length of the inhaler body. The inhaler 50 can have a body that is a portable relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler 50 can also include a display and a user input. The user input may include a "+" and a "−" input key (not shown). The user input can comprise contact pads, a touch screen or other input means, including a numeric entry device which can be used to track the amount of unitized bolus amounts of a target bolus amount of a drug needed by a user.

As shown in FIG. 2A, the inhaler 50 can include a circuit 50*c* that controls certain operations of the inhaler 50. The circuit 50*c* can include a power source and a controller. The controller may, in some embodiments, control the activation of a vibrator 80 that is in communication with the dry powder during inhalation to promote release and/or fluidization of the dry powder during inhalation drug delivery.

The inhaler 50 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 50 can be configured to communicate with a clinician or pharmacy for refills and/or patient compliance. The inhaler 50 may also include a second peripheral device communication port (not shown).

In some embodiments, the controller can include computer program code and/or computer applications that communicate additional data to a user (optionally to the display) as noted above and/or communicate with another remote device (the term "remote" including communicating with devices that are local but typically not connected during normal inhalant use) device.

In some embodiments, the controller can be in communication with the vibrator 80, which can generate powder specific excitation signals. The controller can be programmed with or in communication with an electronic library of a plurality of desired dry powder excitation signals that can be automatically selected by the controller based on the data relayed and carried by the drug containment system 10 corresponding to the drug type/drug disposed therein. In this way, customized drug signals can be used to fluidize the dry powder. In other embodiments, the dry powder excitation signal can be carried on the electronic memory (not shown) held on the drug containment system itself, and the controller can be configured to output the signal to the vibrator 80 operatively associated with the dry powder. Examples of excitation signals and selection methodology are described in co-pending U.S. Patent Application Publication Nos. 2004-0025877-A1 and 2004-0123864, the contents of which are hereby incorporated by reference as if recited in full herein. For example, the excitation signals can be powder specific and employ a carrier frequency modulated by one or more modulating frequencies (that may be amplitude modulating frequencies) that can facilitate fluidic and reliable flow of the dry powder.

The vibratory signal can include a carrier frequency that may be between about 50 Hz to about 1000 Hz, and typically is between about 100 Hz-1000 Hz. The carrier frequency may be modified by one or more low modulating frequencies (typically between about 10-200 Hz). The frequency of the vibration can be modified to match or correspond to the flow characteristics of the dry powder substance held in the package to attempt to reach a resonant frequency(s) to promote uniform drug dispersion into the body. In some embodiments, a non-linear powder-specific dry powder vibratory energy signal comprises a plurality of selected frequencies that can be generated (corresponding to the particular dry powder(s) being currently dispensed) to output the particular signal corresponding to the dry powder(s) then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may include a plurality of (typically at least three) superpositioned modulating frequencies and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

The vibrator 80 can be any suitable vibrator configuration. The vibrator 80 can be configured to vibrate the dry powder in the airflow path. In some embodiments, the vibrator 80 can be configured to vibrate the drug compartment holding the dry powder. Examples of vibrators include, but are not limited to, one or more of: (a) ultrasound or other acoustic or sound-based sources (above, below or at audible wavelengths) that can be used to instantaneously apply non-linear pressure signals onto the dry powder; (b) electrical or mechanical deflection of the sidewalls and/or floor of the inhalation flow channel and/or drug compartment, which can include magnetically induced or caused vibrations and/or deflections (which can use electro or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electro-mechanical vibratory devices are described in U.S. Pat. Nos. 5,727,607, 5,909,829 and 5,947,169, the contents of which are incorporated by reference as if recited in full herein. In some particular embodiments, the vibrator 80 includes at least one piezoelectric element, such as a piezoceramic component, and/or a piezoelectric polymer film.

In certain embodiments, the inhaler 50 can include visible indicia and/or can be configured to provide audible alerts to warn a user that a DCS is misaligned in the inhaler 50 and/or that a dose was properly (and/or improperly) inhaled or released from the inhaler device. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path in an inhaler and configured to be in communication with a digital signal processor or microcontroller each held in or on the inhaler. In operation, the sensor can be configured to detect a selected parameter, such as a difference in weight, a density in the exiting aerosol formulation, and the like, to confirm that the dose was released.

The circuit 50*c* (FIG. 2A) can include a processor (such as a digital signal processor) and electronic memory. The electronic memory can include, but is not limited to, cache, ROM, PROM, EPROM, EEPROM, flash memory, SRAM, and DRAM. The circuit 50*c* can include a library module of a priori signals for different drugs, the appropriate one of which can be selected for operation by the inhaler depending on the drug(s) in the package. The module may be programmed into the memory.

While the present invention is illustrated, for example, with reference to particular divisions of programs, functions and memories, the present invention should not be construed as limited to such logical divisions. Thus, the present invention(s) should not be construed as limited to the configurations shown and described, as the invention(s) is intended to encompass any configuration capable of carrying out the operations described herein.

Certain embodiments may be particularly suitable for dispensing medication to diabetic patients, cystic fibrosis patients and/or patients having diseases or impairments where variable bolus medicaments are desired. Other embodiments may be particularly suitable for dispensing narcotics, hormones and/or infertility treatments.

The present invention is explained in greater detail in the following non-limiting Examples.

EXAMPLES

FIG. 30 is a graph illustrating the percentage of FPF emitted as a function of resistance (sqrt[cm $H_2O$])/lpm) (where “lpm” means “liters per minute”) taken under transient flow conditions and plotted for various shapes of fins and mesh configurations described herein with a dry powder formulation of a certain dose amount (taken at 60 lpm, with no vibratory signal). It is noted that the design numbers used in FIGS. 30 and 31 correspond to each other. In addition, the shapes and designs labeled in FIGS. 30 and 31 have been described above in the specification. However, the design numbers used in the graph of FIG. 30 and the table of FIG. 31 do not necessarily represent or correspond to the design numbers or shape numbers (or order) of the fins or mesh previously described above. The same dose amount, type of dry powder and air path size was used to obtain the data shown in FIG. 30.

It is anticipated that different fin and/or mesh configurations may be used for different formulations of dry powder (types, quantities and the like). It is also anticipated that different resistance performance may be desired for different diseases or conditions and the fins/mesh for the inhalers can be configured for their target disease or condition. For example, it may be desirable to increase resistance for insulin delivery to slow intake at delivery. In contrast, it may be desirable to have reduced resistance for asthma where the lungs may be compromised and/or inspiratory ability may be decreased.

It is contemplated that the fin or mesh design can be chosen based on the drug being delivered to give the desired resistance and a suitable FPF. For example, there are four designs shown in FIG. 30 that have an FPF between 70-80%, with the respective resistance varying from less than 0.070 to above about 0.090. This can allow some flexibility in customizing an inhaler to a particular drug or condition/impairment. Surprisingly, misaligned (offset) arrays of fins may provide similar or less resistance with similar FPF than aligned arrays. Also, it is noted that mesh designs provide relatively low resistance but the cone mesh shapes have increased FPF over the flat meshes tested according to the experimental data shown in FIG. 30.

FIG. 31 includes Table I of exemplary fin data corresponding to fin and mesh shapes described herein. The fin area data corresponding to the % airpath blocked for fins was taken as the projected area of the fins, i.e., as if the fins were in a plane looking identical to the way they look when viewed from the end of a tube. The area was calculated using Pro/ENGINEER, a CAD modeling program that calculates area based on defined geometric and size inputs and the like. The “% airpath blocked” for flat mesh designs was calculated using the Pro/ENGINEER modeling program. The % airpath appearing open is the difference between the overall airpath and the % of the airpath blocked by the fin/mesh configurations.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A dry powder inhaler comprising:

an inhaler body with an inspiratory flow path therein; and at least one fin residing in the inspiratory flow path, the at least one fin comprising at least two edges that converge to define a point, the at least one fin being configured to generate a plurality of point-induced and edge-induced flow vortices of air and dry powder in response to inspiratory effort by a user, wherein some of the flow vortices have an axis of rotation that extends in an inspiratory flow direction and some of the flow vortices have an axis of rotation that is substantially orthogonal to the inspiratory flow direction.

2. An inhaler according to claim 1, wherein the at least one fin comprises a plurality of axially spaced apart fins, each statically residing in the inspiratory flow path and configured to extend from a boundary surface across a sub-portion of a width of the inspiratory flow path thereat.

3. An inhaler according to claim 1, further comprising a mouthpiece residing downstream of the at least one fin, in-line with the inspiratory flow path, wherein the inhaler body has a closed outer surface enclosing the at least one fin so that ambient air enters upstream of the at least one fin, wherein the at least one fin is a plurality of fins, each fin having a body portion that inclines inwardly at an acute angle in a primary direction of inspiratory flow from a bounding surface, the fins configured to define at least one point and two edges that all reside in the inspiratory flow path that generate the flow vortices.

4. An inhaler according to claim 3, wherein the fins are arranged as at least two offset fin arrays, such that a first fin array has the fins circumferentially spaced apart with spaces between neighboring fins and a second axially spaced apart fin array has the fins circumferentially spaced apart with a respective fin of the second fin array aligned with a respective space of the first fin array.

5. An inhaler according to claim 3, wherein the fins are arranged as at least two aligned axially spaced apart fin arrays.

6. An inhaler according to claim 3, wherein at least a first plurality of the fins are sized using a mathematical ratio of 1.618 where A is to B as B is to C with "C" being a total cross sectional surface area of the inspiratory flow path at a first location defined by where the first plurality of fins axially terminate in a downstream direction of the flow path, "A" being the surface area of a plurality of fins at the first location, and "B" being the remaining area of the cross sectional surface area of the flow path.

7. An inhaler according to claim 6, wherein the first plurality of fins are three circumferentially spaced apart fins that incline from the bounding surface at about 45 degrees.

8. An inhaler according to claim 3, further comprising a mouthpiece residing downstream of the at least one fin, in-line with the inspiratory flow path, wherein the inhaler body has a wall with a closed outer surface enclosing the at least one fin so that ambient air enters upstream of the at least one fin, wherein at least some of the fins are generally triangularly shaped to have two long edges that converge to an innermost point that resides in the inspiratory airflow path, and wherein the long edges and points of respective fins all extend inwardly from the wall as free end portions thereof.

9. An inhaler according to claim 3, further comprising a mouthpiece residing downstream of the at least one fin, in-line with the inspiratory flow path, wherein the inhaler body has a wall with a closed outer surface enclosing the at least one fin so that ambient air enters upstream of the at least one fin, wherein the fins are substantially triangular with at least one point extending in the inspiratory airflow path, and wherein long edges and points of respective fins all extend inwardly a distance from the wall.

10. An inhaler according to claim 1, wherein the at least one fin is a plurality of fins that are held by a cylindrical insert with an outer wall that abuts an inner wall of the inhaler, wherein the fins comprise at least one array of a plurality of circumferentially spaced apart fins and a plurality of longitudinally spaced apart fins, wherein the fins have an outermost portion attached to the cylindrical insert outer wall and an opposing innermost portion, and wherein the fins angle inward so that the innermost end portion is a free end with the at least two edges that converge to define the point that resides closer to a mouthpiece of the inhaler, and wherein the at least one array includes a first array configured so that respective fins of the first array all extend from a common axial wall location inward with a common length.

11. An inhaler according to claim 1, wherein the fins comprise at least three circumferentially spaced apart fins configured so that respective fins of the first array all extend from a common axial wall location inward and a plurality of longitudinally spaced apart fins, wherein the fins have an outermost portion and an opposing innermost portion, and wherein the fins angle inward from a bounding wall toward a mouthpiece of the inhaler so that the innermost end portion resides closer to a mouthpiece of the inhaler.

12. An inhaler according to claim 1, further comprising a malleable substantially conical or concave body with apertures, the body portion having a larger upstream portion and a smaller downstream portion in the direction of flow, wherein the malleable body holds the at least one fin.

13. The inhaler of claim 1, further comprising dry powder medication held in the inhaler body, and wherein the inhaler operates to generate the flow vortices using only user inspiratory efforts without a pressurized canister for propellant.

14. The inhaler of claim 1, wherein the fins have a primary surface with first and second pairs of innermost edges that converge to respective first and second points, the primary surface oriented in the inspiratory flow path so that the first and second points reside at a common axial location.

* * * * *